(12) United States Patent
Wu

(10) Patent No.: US 9,487,539 B2
(45) Date of Patent: Nov. 8, 2016

(54) COMPOUNDS AND THERAPEUTIC USE THEREOF FOR PROTEIN KINASE INHIBITION

(71) Applicant: Zhanggui Wu, Brookline, MA (US)

(72) Inventor: Zhanggui Wu, Brookline, MA (US)

( * ) Notice: Subject to any disclaimer, the term of this patent is extended or adjusted under 35 U.S.C. 154(b) by 0 days.

(21) Appl. No.: 14/333,529

(22) Filed: Jul. 17, 2014

(65) Prior Publication Data

US 2015/0072987 A1 Mar. 12, 2015

Related U.S. Application Data

(62) Division of application No. 13/496,494, filed as application No. PCT/US2010/049199 on Sep. 17, 2010, now Pat. No. 8,815,863.

(60) Provisional application No. 61/243,549, filed on Sep. 18, 2009.

(51) Int. Cl.
*C07D 495/04* (2006.01)
(52) U.S. Cl.
CPC .................................. *C07D 495/04* (2013.01)
(58) Field of Classification Search
CPC .... A01N 43/58; A61K 31/50; C07D 237/26; C07D 459/02
USPC .......................................... 514/250; 544/233
See application file for complete search history.

(56) References Cited

U.S. PATENT DOCUMENTS 8,815,863 B2 * 8/2014 Wu ............................... 514/250

FOREIGN PATENT DOCUMENTS

JP 2008-534664 A 8/2008
WO WO-2009-092278 7/2009

OTHER PUBLICATIONS

Pinnedo et al. (2000).*
McMahon et al. (2000).*

* cited by examiner

*Primary Examiner* — Paul V Ward
(74) *Attorney, Agent, or Firm* — Kening Li; Miller Canfield

(57) ABSTRACT

Novel compound having the following formula:

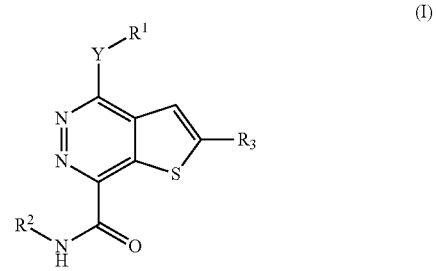

wherein Y is N, O, or S. Also disclosed are a pharmaceutical compositions comprising the same, methods for treating cancer using the same, and methods for the synthesis of the same. The novel compounds of the present invention are found to inhibit protein kinases, especially Checkpoint kinase Chk1/Chk2.

11 Claims, 1 Drawing Sheet

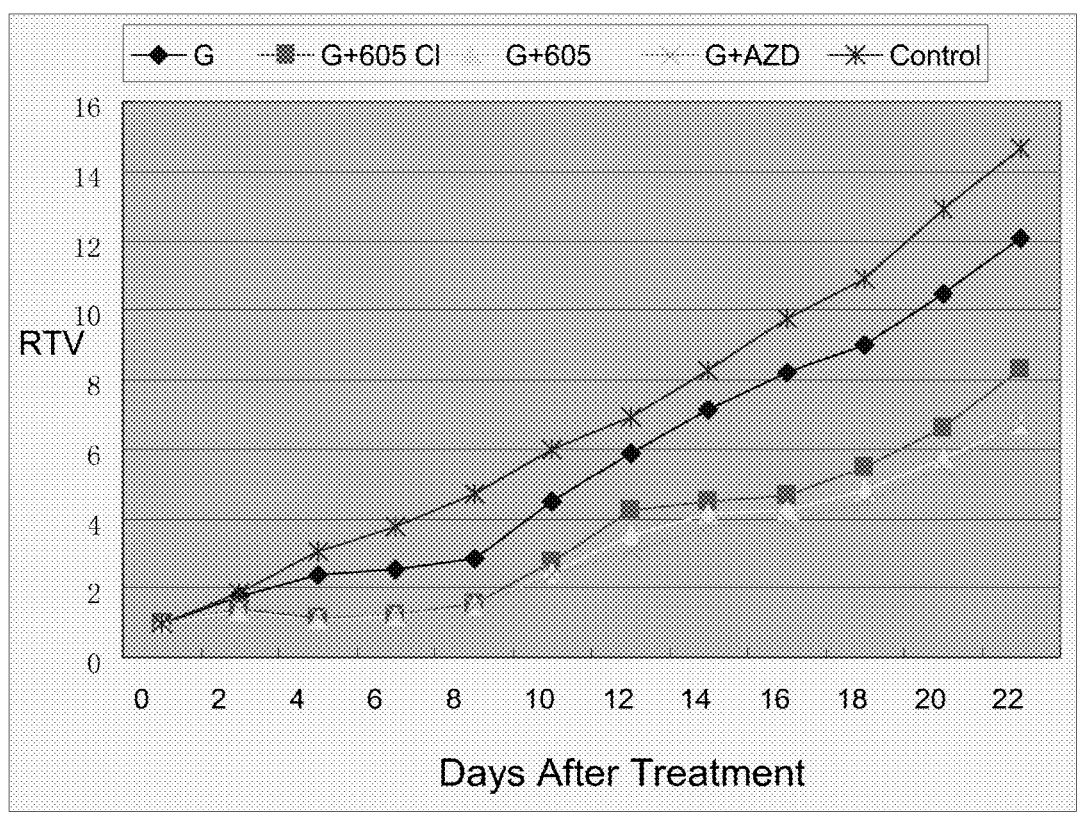

COMPOUNDS AND THERAPEUTIC USE THEREOF FOR PROTEIN KINASE INHIBITION

CROSS REFERENCE TO RELATED APPLICATIONS

This is a divisional application of U.S. application Ser. No. 13/496,494 filed on May 16, 2012 claiming priority to U.S. Patent Application No. 61/243,549, filed on Sep. 18, 2009, the entire disclosure of which is incorporated herein by reference.

FIELD OF THE INVENTION

The invention is related to methods and compositions for modulating the activities of check point kinase 1 (CHK1) and Checkpoint kinase 2 (CHIC), and receptor tyrosine kinase and non-receptor tyrosine kinase. More specifically, the present invention relates to the preparation and use of inhibitors of the above enzymes.

BACKGROUND OF THE INVENTION

The etiology of cancer is extremely complex, and remains poorly understood. What is known is that cancers are intimately related to both environmental factors as well as internal factors of the human body. About three quarters of cancers can be attributed to external, environmental causes. Cancers continue to pose great threat to humanity, and worldwide at least 5 million people die from cancer annually. Currently available methods of treatment, such as surgery, radiotherapy, chemotherapy all have their limitations.

Of the available cancer treatment and prevention methods, chemical agents remain the most effective.

One category of cancer chemotherapy agents are the inhibitors or antagonists of both receptor tyrosine kinases and non-receptor tyrosine kinases. Specific targets include vesicular endothelial growth factor receptor (VEGFR), epidermal growth factor receptor (EGFR), HER2 (human epidermal growth factor receptor 2), SRC, JAK (Janus kinase) and TEK.

Certain thieno-pyridazine compounds have been found to have anti-tumor activities. For example, WO2005105808 discloses such a compound as an IKK inhibitor:

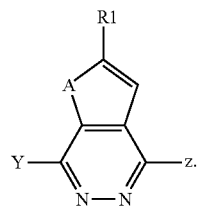

In addition, WO2007424181 discloses compounds that are inhibitors of p38 protease, a type of tyrosine kinase:

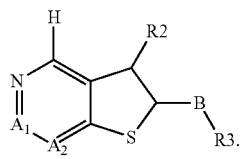

Further, WO 03029241, WO 03028731 and WO2005066163 disclose similar compounds that are inhibitors of CHK1.

Nevertheless, there is a need for more anti-cancer compounds that are inhibitors of tyrosine kinases, especially CHK1/CHK2.

DESCRIPTION OF THE INVENTION

The present invention provides novel inhibitors of certain protein kinases, especially cellular checkpoint kinases (CHK1 and CHK 2), and receptor tyrosine kinase and non-receptor tyrosine kinases, such as VEGFR (Vascular endothelial growth factor receptors), EGFR (epidermal growth factor receptor), HER2 (Human Epidermal growth factor Receptor 2), SRC kinases, JAK kinase and TEK kinases; and serine/threonine kinases such as MEK, JNK, c-MET, AKT, PIM, TIE and PLK.

Checkpoint kinase 1 is an evolutionarily highly conserved protein kinase, and functions to control the progression of cell cycle at the S and G2/M check points. DNA damages activates Chk1, halting the cell cycle and causing the damaged DNA to be repaired. If the DNA damages are too extensive to repair, the cell dies such that the integrity and stability of the genome is maintained. Cancer cells devoid of or defective in Chk1 display many defects in cell cycle control, including decreased cell division rate, lack of reaction to cell cycle check points, and increased sensitivity to DNA damages. Due to its functions in damage repair, Chk1 plays an important role in the cancer ontology, cancer cell death, and cancer drug resistance.

Research on checkpoints of cell cycle regulations revealed that inhibition of CHK1 expression can reverse drug resistance or tolerance of cancer cells, thereby increasing the sensitivity of cancer cells to DNA damage therapy, and dramatically increasing the activities and effectiveness of anti-cancer agents. Most cancers have mutations in p53 that specifically eliminates GUS checkpoint, which can also be a basis for screening for specific anti-cancer agents. Inhibitors of Chk1 kinase may be good candidates for specific anti-cancer agents or for enhancing the activities of other anti-cancer drugs, because Chk1 kinase also regulates the G2/M checkpoint. Even though Chk1 inhibitors themselves may not have strong anti-cancer activities, they may still be able to enhance the anticancer activities of other drugs if used in combination.

The present invention provides novel protein kinase inhibitor compounds or pharmaceutically acceptable salts or derivatives thereof that have anti-cancer activities. The compounds of the present invention are inhibitors of cancer-related protein kinases such as CHK1 and CHK2, and can also increase or enhance the activities of other anti-cancer agents. The present invention also provides methods of preparing the compounds, pharmaceutical compositions comprising the compounds, and method of using the compounds in the preparation of pharmaceutical compositions for inhibiting cell multiplication or cell proliferation in warm blooded animals such as humans.

Cell cycle arrest-related or cell proliferation-related diseases that can be treated with compounds of the present invention or pharmaceutical compositions comprising the same include cancer (including solid tumors and leukemia), fibrosis and related diseases, psoriasis, rheumatoid arthritis, Kaposi sarcoma, acute and chronic renal diseases, atheroma, atherosclerosis, artery stenosis, autoimmune diseases, acute or chronic inflammation, bone disease, and eye diseases caused by retinal neo-angiogenesis.

The novel compounds of the present invention generally have Formula I described below.

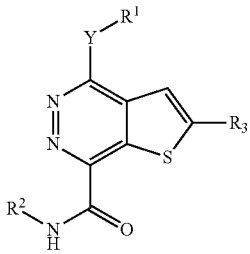
(I)

where
Y=NH, O, or S,
$R^1$=selected from following groups:

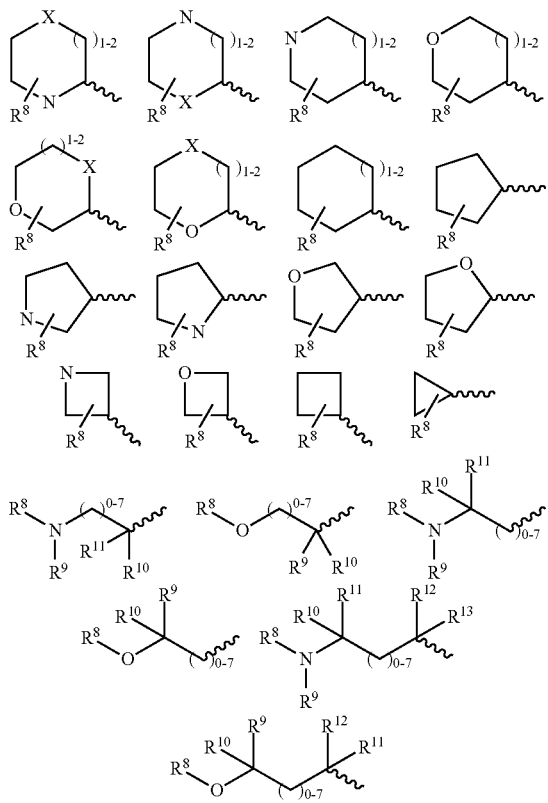

wherein X=CH$_2$, NH, S, or O,
$R^8$=—H, —NH$_2$, —OH, —N(R$^4$, R$^5$), —C(R$^4$R$^5$)$_{1-7}$NR$^6$R$^7$, —C(R$^4$R$^5$)$_{1-7}$OR$^6$, or —N(R$^4$)NR$^5$R$^6$, wherein R$^4$, R$^5$, R$^6$, R$^7$=H, alkyls (C$_1$-C$_6$), cycloalkyls (C$_3$-C$_8$) with or without nuclear heteroatoms such as O, S, and N, aryls (either unsubstituted or substituted aromatics), or heteroaromatics (either unsubstituted or substituted heteroaromatics),
R$^9$, R$^{10}$, R$^{11}$, R$^{12}$, and R$^{13}$=H, alkyls (C$_1$-C$_6$), cycloalkyls (C$_3$-C$_8$) with or without nuclear heteroatoms such as O, S or N; aryls (either unsubstituted and substituted aromatics), or heteroaromatics (either unsubstituted or substituted heteroaromatics),
$R^2$, is selected from a group consisting of H, OH, NH$_2$, OR$^{14}$, NR$^{14}$R$^{15}$, alkyl, aryl, heteroaryl, cycloalkyl, arylalkyl, heterocyclyl, heterocyclylalkyl, alkenyl, and alkynyl, wherein R$^{14}$, R$^{15}$=H, alkyls (C$_1$-C$_6$), cycloalkyls (C$_3$-C$_8$) with or without nuclear heteroatoms such as O, S, N, aryls (either unsubstituted or substituted aromatics), or heteroaromatics (either unsubstituted or substituted heteroaromatics), and
$R^3$ is selected from a group consisting of H, alkyl, aryl, heteroaryl, cycloalkyl, arylalkyl, heterocyclyl, heterocyclylalkyl, alkenyl, and alkynyl. Specifically R$^3$ is selected from the following groups:

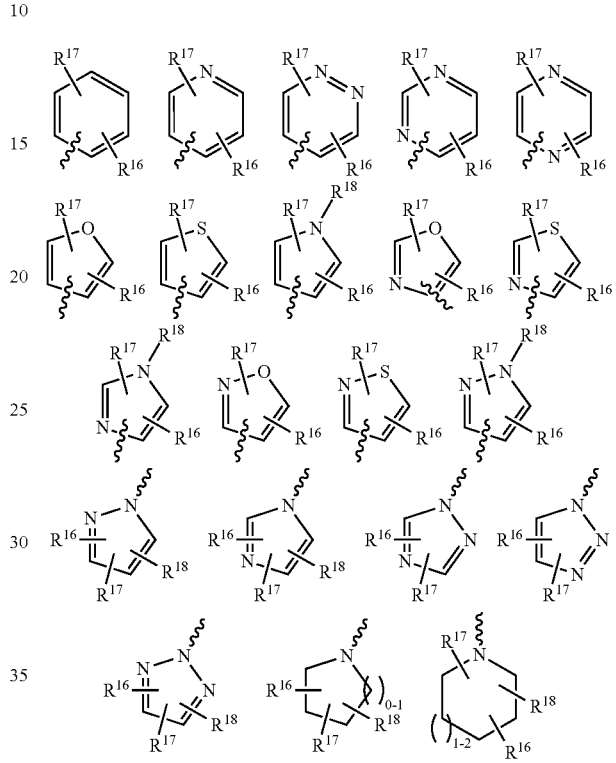

wherein $R^{16}$, $R^{17}$, and $R^{18}$ are selected from following groups: H; heteroatom such as F, Cl, Br, I; alkyl(C$_1$-C$_8$); cycloalkyl(C$_3$-C$_8$) without or with substitutions, wherein a substitution is selected from the group consisting of alkyls (C$_1$-C$_8$), cycloalkyls (C$_3$-C$_8$), aryls, heteroaryls; —OR$^{19}$; —SR$^{19}$; —NR$^{19}$R$^{20}$; —S(O)R$^{19}$; —S(O)$_2$R$^{19}$; —S(O)$_2$NR$^{19}$R$^{20}$; —C(O)NR$^{19}$R$^{20}$); —N(R$^{19}$)C(O)R$^{20}$; —N(R$^{19}$)S(O)$_2$R$^{20}$; —N(R$^{19}$)C(O)N(R$^{20}$R$^{21}$); N(R$^{19}$)C(O)OR$^{20}$; aryl with or without substitution, heteroaryl with or without substitution, aryalkyl with or without substitution, heterocyclyl with or without substitution, heterocyclylalkyl with or without substitution; alkenyl with or without substitution, and alkynyl with or without substitution;
where $R^{19}$, $R^{20}$, and $R^{21}$ are independently chosen from H, alkyl(C$_1$-C$_8$), cycloalkyls (C$_3$-C$_8$), aryl with or without substitution, alkylaryl with or without substitutions, heteroaryl with or without substitution,
or R$^{16}$, R$^{17}$, and R$^{21}$ can be part of a fused ring containing 0-3 heteroatoms selected from N, O, and S.

The term "heteroaryl" as used herein refers to aromatic rings in which one or more carbon atoms of the aromatic ring(s) are substituted by a heteroatom such as nitrogen, oxygen or sulfur. Heteroaryl refers to structures which may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are encompassed by the term "heteroaryl."

Substituted heteroaryl refers to heteroaryl as described wherein the heteroaryl nucleus is substituted with one or more functional groups such as lower alkyl, acyl, halogen, alkylhalos, hydroxy, amino, alkoxy, alkylamino, acylamino, acyloxy, mercapto, etc. Thus, substituted analogues of heteroaromatic rings such as thiophene, pyridine, isoxazole, phthalimide, pyrazole, indole, furan, etc. or benzo-fused analogues of these rings are encompassed by the term "substituted heteroaryl."

The term "heterocyclic" is used herein to describe a saturated or unsaturated non-aromatic group having a single ring or multiple condensed rings from 1-12 carbon atoms and from 1-4 heteroatoms selected from nitrogen, sulfur or oxygen within the ring. Such heterocycles are, for example, tetrahydrofuran, morpholine, piperidine, pyrrolidine, etc.

The term "substituted heterocyclic" as used herein describes a subset of "heterocyclic" wherein the heterocycle nucleus is substituted with one or more functional groups such as lower alkyl, acyl, halogen, alkylha.los, hydroxy, amino, alkoxy, alkylamino, acylamino, acyloxy, mercapto, etc.

The above compounds can be prepared as illustrated in the following general schemes:

Scheme 1:

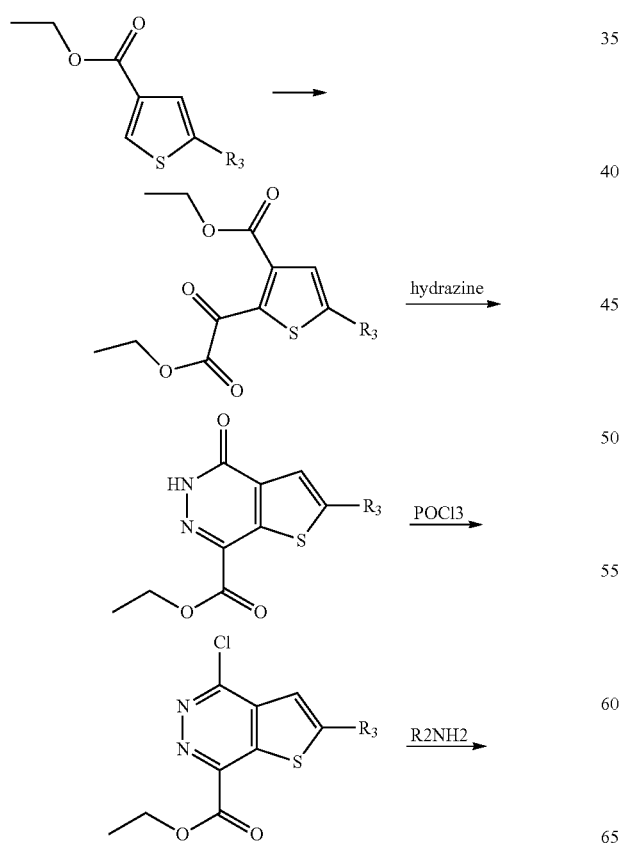

Scheme 2:

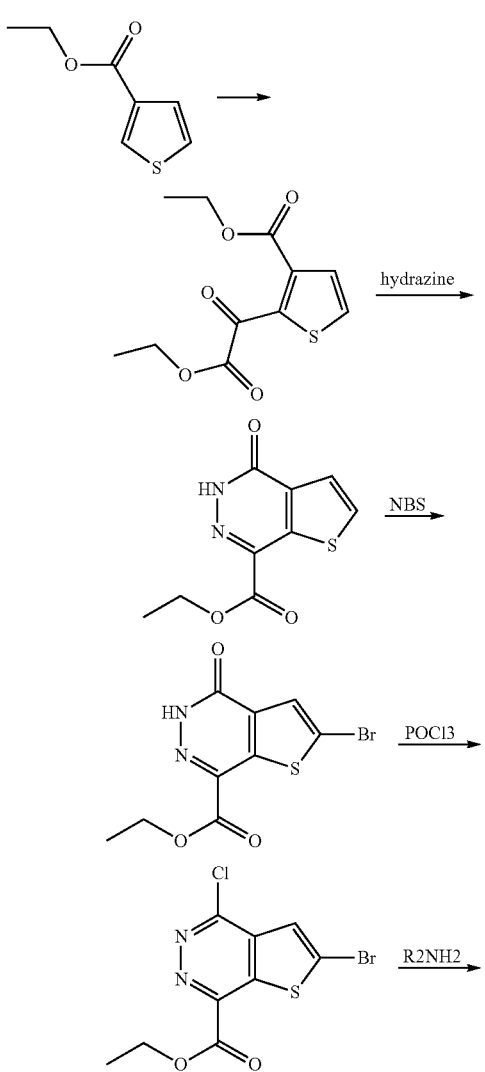

-continued

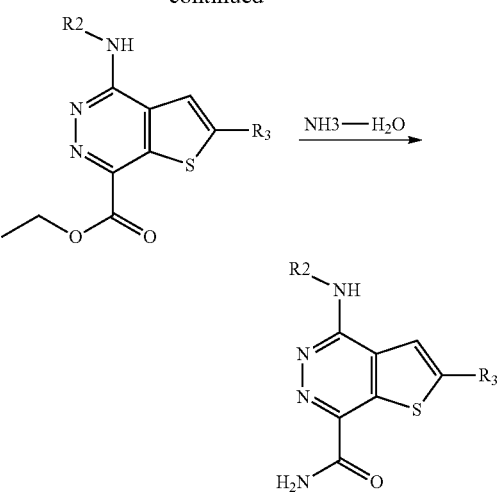

-continued

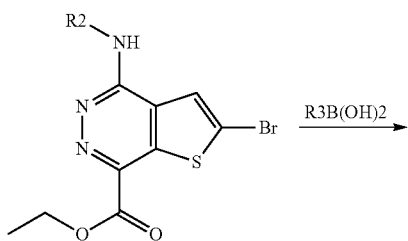

Scheme 3:

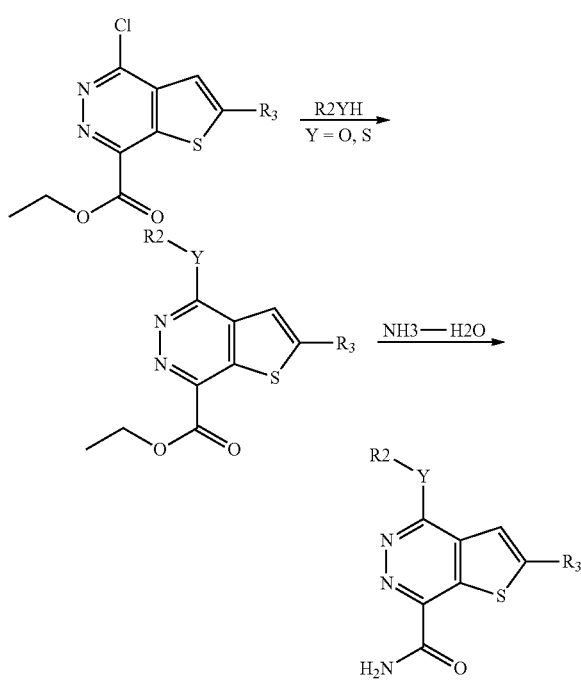

In a preferred embodiment, the novel compounds of the present invention have a Formula II:

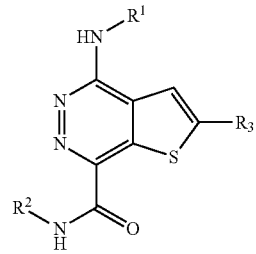

(II)

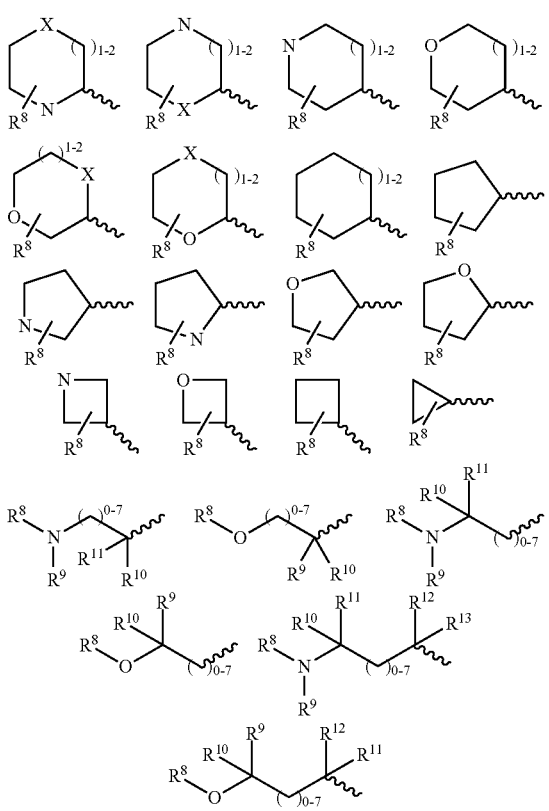

wherein,
R¹ is selected from following groups:

where X=CH₂, NH, S, or O;
R⁸=—H, —NH₂, —OH, —N(R⁴,R⁵), —C(R⁴R⁵)$_{1-7}$ NR⁶R⁷, —C(R⁴R⁵)$_{1-7}$OR⁶, —N(R⁴)NR⁵R⁶
R⁴, R⁵, R⁶, R⁷=H, alkyls (C₁-C₆), cycloalkyls (C₃-C₈) with or without nuclear heteroatoms such as O, S, N, aryls (selected from unsubstituted and substituted aromatics), or heteroaromatics (selected from unsubstituted and substituted heteroaromatics)
R⁹, R¹⁰, R¹¹, R¹², R¹³=H, alkyls (C¹-C⁶), cycloalkyls (C³-C⁸) with or without nuclear heteroatoms such as O, S, N, aryls (selected from unsubstituted and substituted aromatics) heteroaromatics (selected from unsubstituted and substituted heteroaromatics),
R² is selected from a group consisting of H, OH, NH₂, OR¹⁴, NR¹⁴R¹⁵, alkyl, aryl, heteroaryl, cycloalkyl, arylalkyl, heterocyclyl, heterocyclylalkyl, alkenyl, alkynyl, wherein R¹⁴ and R¹⁵ are H, alkyl(C₁-C₆); cycloalkyl(C₃-C₈) without or with substitutions with heteroatoms such as O, S, and N; or a substituted or un-substituted aromatic ring, R³ is selected from a group consisting of H, alkyl, aryl, heteroaryl, cycloalkyl, arylalkyl, heterocyclyl, heterocyclylalkyl, alkenyl, and alkynyl; preferably R³ is selected from the following groups:

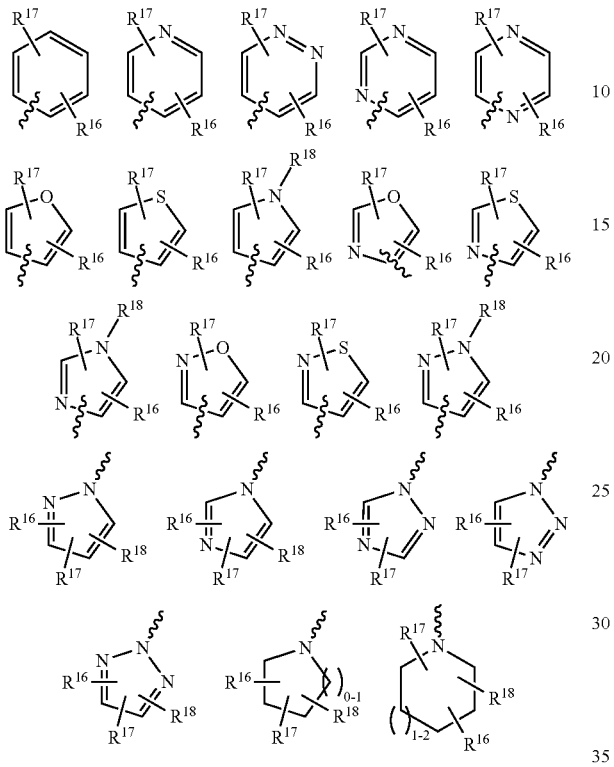

where R¹⁶, R¹⁷ and R¹⁸ are selected from following groups: H; heteroatom such as F, Cl, Br, I; alkyl($C_1$-$C_8$); cycloalkyl ($C_3$-$C_8$) without and with substitutions: substitutions are selected from alkyls ($C_1$-$C_8$), cycloalkyls ($C_3$-$C_8$), aryls, and roaryls; —OR¹⁹; —SR¹⁹; —NR¹⁹R²⁰, —S(O)R¹⁹; —S(O)₂R¹⁹; —S(O)₂NR¹⁹R²⁰; —C(O)NR¹⁹R²⁰; —N(R¹⁹)C(O)R²⁰; —N(R¹⁹)S(O)₂R²⁰; —N(R¹⁹)C(O)N(R²⁰R²¹); —N(R¹⁹)C(O)OR²⁰; Aryl with or without substitution, heteroaryl with or without substitution, aryalkyl with or without substitution, heterocyclyl with or without substitution, heterocyclylalkyl with or without substitution, alkenyl with or without substitution, alkynyl with or without substitution; where R¹⁹, R²⁰ and R²¹ chosen from H, alkyl($C_1$-$C_8$), cycloalkyls ($C_3$-$C_8$), aryl with or without substitution, alkylaryl with or without substitutions, and heteroaryl with or without substitution; or R¹⁶, R¹⁷ and R¹⁸ can be part of ring which is fused containing 0-3 heteroatoms selected from N, O, and S.

The above compounds can be prepared as illustrated in the following general scheme:

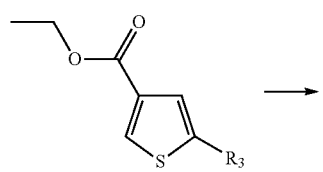

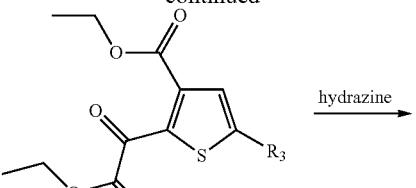

-continued

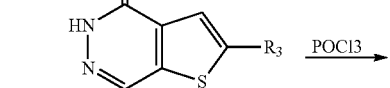

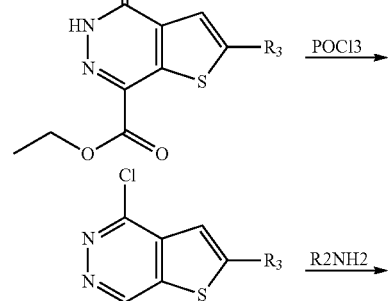

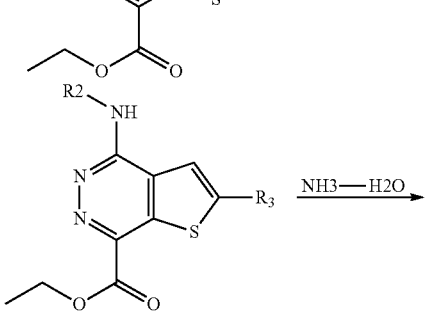

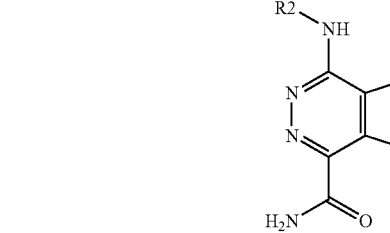

Synthesis of the novel compounds according to the above schemes can be implemented using processes known to those skilled in the art, for example those disclosed in U.S. Pat. Publication No. US2009-0275585A1 and WO2005105808, which are incorporated herein by reference in their entirety.

The novel compounds of the present invention are inhibitors of protein kinases including CHK1 and CHK2, and can prevent DNA damage repair mechanism from arresting the cell cycle at the G2/M checkpoint. Thus these compounds have anti-proliferative (e.g. anti-cancer) activities, and can also be sued in combination with other anti-cancer agents, to enhance their anti-cancer effects. The compounds are thus useful as cancer therapeutic agents for treating humans and animals. The present invention further includes methods for making the novel compounds, pharmaceutical compositions comprising the compounds, the use of the compounds or its salts or prodrugs for the manufacture of pharmaceutical compositions, as well as methods of treatment using the pharmaceutical composition.

In another embodiment, the present invention provides a pharmaceutical composition comprising a compound described above and a pharmaceutically acceptable adjuvant or excipient, and a method for treating cancer by administering an effective amount of the pharmaceutical composition to a patient in need thereof. Administration of an "effective amount" or a "therapeutically effective amount" of a compound of the present invention means an amount that is useful, at dosages and for periods of time necessary to achieve the desired result. The therapeutically effective amount of a compound in accordance with the present invention may vary according to factors, such as the disease state, age, sex, and weight of the subject. Dosage regimens in the patient may be adjusted to provide the optimum therapeutic response. For example, several divided doses may be administered daily or the dose may be proportionally reduced as indicated by the exigencies of the therapeutic situation. In the context of the present invention, a "pharmaceutically acceptable salt," refer to salts prepared from pharmaceutically acceptable, non-toxic acids.

The pharmaceutical compositions according to the invention can be present and administered as liquid, semi-solid or solid medicament forms and in the form of e.g. injection solutions, drops, juices, syrups, suspensions, sprays, granules, tablets, pellets, patches, capsules, plasters, suppositories, ointments, creams, lotions, gels, emulsions or aerosols, and comprise a compound of the present invention, and pharmaceutical auxiliary substances according to the galenical form, such as e.g. carrier materials, fillers, solvents, diluents, surface-active substances, dyestuffs, preservatives, disintegrating agents, anti-friction agents, lubricants, flavorings and/or binders. These auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethylcellulose, cellulose acetate, shellac, cetyl alcohol, polyvinylpyrrolidone, paraffins, waxes, naturally occurring and synthetic gums, acacia gum, alginates, dextran, saturated and unsaturated fatty acids, stearic acid, magnesium stearate, zinc stearate, glyceryl stearate, sodium lauryl sulfate, edible oils, sesame oil, coconut oil, ground nut oil, soya bean oil, lecithin, sodium lactate, polyoxyethylene and -propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite. The choice of auxiliary materials and the amounts thereof to be employed depend on whether the medicament is to be administered orally, perorally, subcutaneously, parenterally, intravenously, intraperitoneally, intradermally, intramuscularly, intranasally, buccally, rectally or locally, for example to infections on the skin, the mucous membranes and the eyes. Formulations in the form of tablets, coated tablets, capsules, granules, drops, juices and syrups are suitable, inter alia, for oral administration, and solutions, suspensions, easily reconstitutable dry formulations and sprays are suitable for parenteral, topical and inhalatory administration. A compound according to the invention in a depot in dissolved form or in a patch, optionally with the addition of agents which promote penetration through the skin, are suitable formulations for percutaneous administration. Formulation forms which can be used orally or percutaneously can release the compound according to the invention in a delayed or controlled manner.

The medicaments and pharmaceutical compositions according to the invention are prepared with the aid of agents, devices, methods and processes which are well-known in the prior art of pharmaceutical formulation, such as are described, for example, in Remington's Pharmaceutical Sciences, 18th ed., Mack Publishing Co., Easton, Pa. (1990), in particular in part 8, sections 76 to 93.

Thus for a solid formulation, such as a tablet, the active compound of the medicament, can be mixed with a pharmaceutical carrier, e.g. conventional tablet constituents, such as maize starch, lactose, sucrose, sorbitol, talc, magnesium stearate, dicalcium phosphate or gum, and pharmaceutical diluents, such as e.g. water, in order to form a solid preformulation composition which comprises a compound according to the invention or a pharmaceutically acceptable salt thereof in homogeneous distribution. Homogeneous distribution here is understood as meaning that the active compound is distributed uniformly over the entire preformulation composition, so that this can easily be divided into unit dose forms of the same action, such as tablets, pills or capsules. The solid preformulation composition is then divided into unit dose forms. The tablets or pills of the medicament according to the invention or of the compositions according to the invention can also be coated, or compounded in another manner in order to provide a dose form with delayed release. Suitable coating compositions are, inter alia, polymeric acids and mixtures of polymeric acids with materials such as e.g. shellac, cetyl alcohol and/or cellulose acetate.

The amount of active compound to be administered to the patient varies and depends on the weight, age and disease history of the patient, as well as on the mode of administration, the indication and the severity of the disease. A range of does, for example 0.1 to 5,000 mg/kg, in particular 1 to 500 mg/kg, preferably 2 to 250 mg/kg of body weight of a compound according to the invention are usually administered.

The pharmaceutical composition of the present invention may be administered enterally (such as orally or via rectal administration), externally, or parenterally e.g. via injection. Suitable formulations include tablets (such as conventional tablets, buccal tablets, sublingual tablet, oral cavity patch, chewable tablet, effervescent tablet, vaginal tablet, vaginal effervescent tablet, sustained-release tablet, controlled release tablet, enteric coated tablet, buccal rapid-release tablet), capsules (hard capsules, soft capsules, sustained-release capsules, controlled-release capsules, enteric-coated capsules, etc), pills (dripping pills, sugar coated pills, pellets), oral liquid (oral solution, oral suspension, oral emulsion, etc), granules (suspension granules, soluble granules, effervescent granules, gastro-resistant granules, sustained-release granules, controlled-release granules, etc), injection (injectable solution, injectable emulsion, injectable suspension), intravenous infusion, powder for injection, concentrated solution for injection, implants, etc, and other medicament form such as suppositories, aerosol, aerosol powder, spray, gel, pellicles, patches, etc.

Compounds of the present invention may be incorporated into biodegradable polymers allowing for sustained release of the compound, the polymers being implanted in the vicinity of where drug delivery is desired, for example, at the site of a tumor or implanted so that the compound is slowly released. The biodegradable polymers and their use are described, for example, in detail in Brem et al., J. Neurosurg. 74:441-446(1991). Osmotic mini pumps may also be used to provide controlled delivery.

Toxicity and therapeutic efficacy of such compounds can be determined by standard pharmaceutical procedures in cell cultures or experimental animals, e.g., for determining the LD50 (the dose lethal to 50% of the population) and the ED50 (the dose the therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized.

Pharmaceutical composition of the present invention is suitable for treating cancers and the related diseases, and may be used alone or in combination with other anti-cancer drugs. An ordinarily skilled person in the art will be able to determine the suitable dosage for the treatment, depending on the types of disease to be treated, the formulation and the conditions of the patient.

The compounds of this invention can be used to prevent or treat abnormal cell proliferation, especially those found in tumors or cancers, including lung cancer, liver cancer, leucocythaemia, osteocarcinoma, pancreas cancer, skin cancer, melanoma, metrocarcinoma, oophoroma, rectal carcinoma, gastric carcinoma, colon cancer, breast carcinoma, *salpinx* carcinoma, endometrium carcinoma, cervix carcinoma, vagina carcinoma, carcinoma of vulva, esophagus carcinoma, small intestine carcinoma, incretion carcinoma, soft tissue sarcoma, urethra carcinoma, prostatic cancer, lymphocytoma, bladder cancer, nephridium cancer, tumors of vertebral column, tumors in the neuroglia of the brain, and pituitary adenoma.

FIG. 1 illustrates the results as shown in Table 4-1 and Table 4-2.

The pharmaceutical composition of the present invention may also be used for the prevention or treatment of autoimmune diseases, inflammation, nerve system diseases, and cardiovascular diseases. Especially, the pharmaceutical compositions of the present invention may be used to treat cell cycle-related or cell proliferation related diseases.

EXAMPLES

Example 1

Synthesis of Compounds of Compound (S)-2-(3-fluorophenyl)-4-(piperidin-3-ylamino)thieno[2,3-d]pyridazine-7-carboxamide Following the following scheme 3, Compound (S)-2-(3-fluorophenyl)-4-(piperidin-3-ylamino)thieno[2,3-d]pyridazine-7-carboxamide was synthesized:

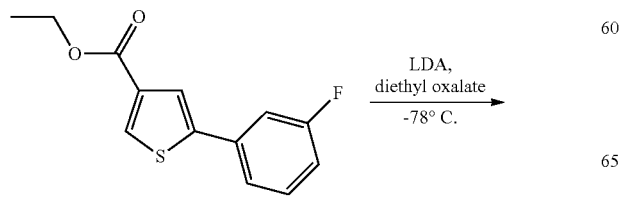

-continued

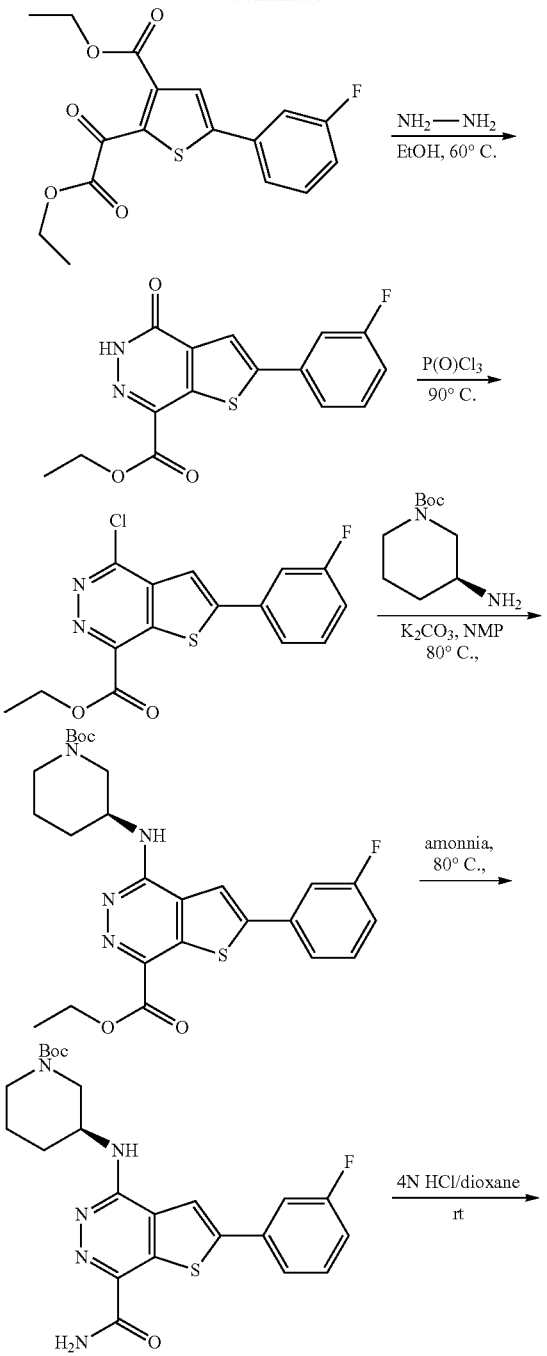

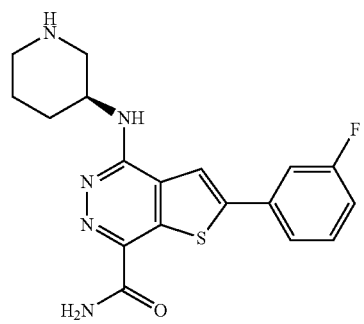

Step 1

The LDA (20 mmol) was added to the solution of thiophene (5.34 g, 20 mmol) and diethyl oxalate in THF (100 mL) at −78° C. dropwise. After the addition, the resulting mixture was allowed to warm to 0° C. and stirred at 0° C. for 30 min. HCl (1N) was added to quench the reaction and extracted with EtOAc. The organics was dried over $Na_2SO_4$ and concentrated. The residue was purified with column gave the product as yellowish solid (7.07 g). HPLC-MS $t_R$=2.39 min ($UV_{254\ nm}$); mass calculated for formula $C_{17}H_{15}FO_5S$ 350.0, observed LCMS m/z 351.0 (M+H).

Step 2

The ketone from step 1 (7.07 g, 19.2 mmol) was dissolved in ethanol (50 mL) and hydrazine (1 mL) was added. The mixture was heated up to 60° C. and stirred for 10 min. Then, the mixture was cooled to room temperature and stirred for another 30 min. The solid was collected by filtration and washed with small amount cold ethanol. The solid was dried under air gave the pure product (6.17 g) as white solid. HPLC-MS $t_R$=1.88 min ($UV_{254\ nm}$); mass calculated for formula $C_{15}H_{11}FN_2O_3S$ 318.0, observed LCMS m/z 319.0 (M+H).

Step 3

The heterocyclic compound from step 2 (2.8 g, 8.8 mmol) was added to $P(O)Cl3$ (20 mL) and the mixture was heated up to 90° C. and stirred at that temperature for 3 hours. The solvent was removed under reduced pressure and the residue was taken up with EtOAc. The solid was filtered off and the organics was concentrated and purified with column (silica gel) gave the product (2.31 g) as yellowish solid. HPLC-MS $t_R$=2.40 min ($UV_{254\ nm}$); mass calculated for formula $C_{15}H_{10}ClFN_2O_2S$ 336.0, observed LCMS m/z 337.0 (M+H).

Step 4

The chloro-compound (336 mg, 1.0 mmol) was dissolved in NMP (5 mL) and $K_2CO_3$ (272 mg, 2.0 mmol) and (S)-tert-butyl 3-aminopiperidine-1-carboxylate (200 mg, 1.0 mmol) was added. The mixture was heated up to 80° C. and stirred for 3 hour. After cooling to room temperature, the mixture was diluted with EtOAc and washed with water, brine and dried over $Na_2SO_4$. After concentration, the crude was purified with column give the product (357 mg). HPLC-MS $t_R$=2.09 min ($UV_{254\ nm}$); mass calculated for formula $C_{25}H_{29}FN_4O_4S$ 500.2, observed LCMS m/z 501.1 (M+H).

Step 5

The (S)-ethyl 4-(1-(tert-butoxycarbonyl)piperidin-3-ylamino)-2-(3-fluorophenyl)thieno[2,3-d]pyridazine-7-carboxylate (50 mg, 0.1 mmol) was mixed with ammonia (4 mL) in a sealed tube at room temperature. The mixture was heated up to 80° C. and stirred overnight. Then the solvent was removed by concentration. The crude product (S)-tert-butyl 3-(7-carbamoyl-2-(3-fluorophenyl)thieno[2,3-d]pyridazin-4-ylamino)piperidine-1-carboxylate was used in the next step directly without further purification. HPLC-MS $t_R$=1.75 min ($UV_{254\ nm}$); mass calculated for formula $C_{23}H_{26}FN_5O_3S$ 471.2, observed LCMS m/z 472.2 (M+H).

Step 6

The crude product from step 5 (S)-tert-butyl 3-(7-carbamoyl-2-(3-fluorophenyl)thieno[2,3-d]pyridazin-4-ylamino)piperidine-1-carboxylate was treated with HCl (4N in dioxane, 3 mL) at room temperature for 30 min. Then the solvent was removed under reduced pressure and the residue was purified with HPLC to obtain the final compound (S)-2-(3-fluorophenyl)-4-(piperidin-3-ylamino)thieno[2,3-d]pyridazine-7-carboxamide. HPLC-MS $t_R$=1.27 min ($UV_{254\ nm}$); mass calculated for formula $C_{18}H_{18}FN_5OS$ 371.1, observed LCMS m/z 372.1 (M+H).

Example 2

Synthesis of Compound 2-(3-fluorophenyl)-4-(piperidin-3-yloxy)thieno[2,3-d]pyridazine-7-carboxamide

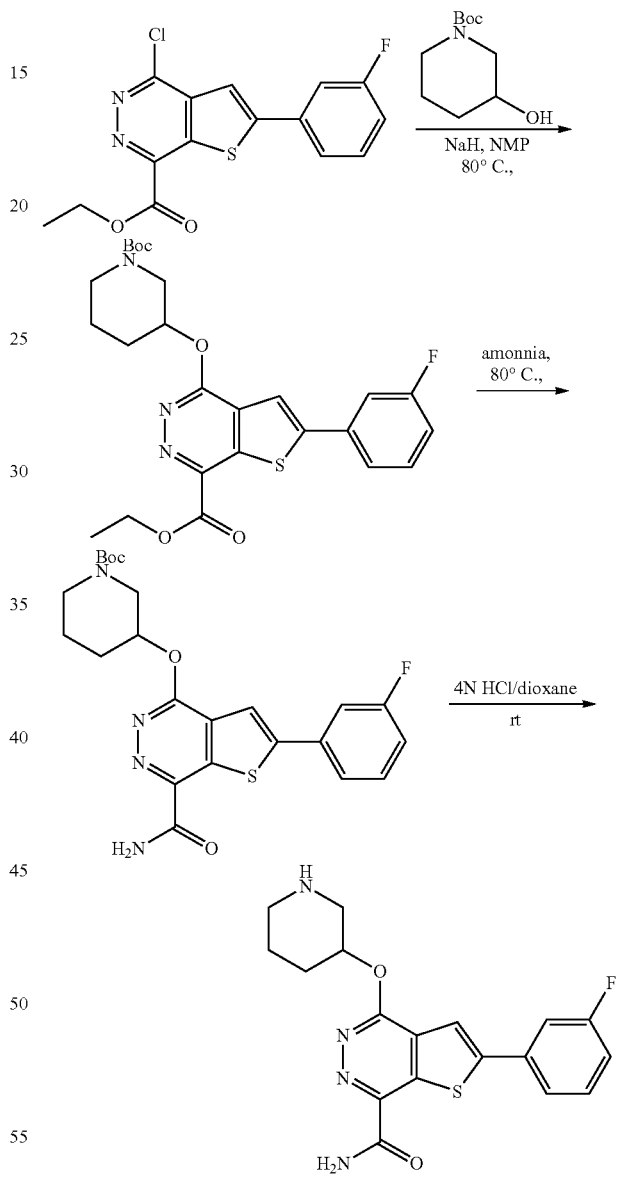

Ethyl 4-chloro-2-(3-fluorophenyl)thieno[2,3-d]pyridazine-7-carboxylate has been made in example 1 step 3.

Step 1 tert-Butyl 3-hydroxypiperidine-1-carboxylate (100 mg, 0.5 mmol) was dissolved in dry NMP (5 mL) and NaH (20 mg, 60% in oil, 0.5 mmol) was added carefully. The mixture was stirred at room temperature for 10 min. Then, ethyl 4-chloro-2-(3-fluorophenyl)thieno[2,3-d]pyridazine-7-carboxylate (130 mg, 0.5 mmol) was added. The mixture was heated up to 80° C. and stirred for 30 min. After cooling to room temperature, EtOAc was added to dilute the reaction and washed with water and brine. The organics was dried over $Na_2SO_4$ and filtered, concentrated. The crude product was purified with column (silica gel) to give the product ethyl 4-(1-(tert-butoxycarbonyl)piperidin-3-yloxy)-2-(3-fluorophenyl)thieno[2,3-d]pyridazine-7-carboxylate (151 mg). HPLC-MS $t_R$=2.17 min ($UV_{254\ nm}$); mass calculated for formula $C_{25}H_{28}FN_3O_5S$ 501.2, observed LCMS m/z 502.2 (M+H).

Step 2

The compound tert-butyl 3-(7-carbamoyl-2-(3-fluorophenyl)thieno[2,3-d]pyridazin-4-yloxy)piperidine-1-carboxylate was prepared with the same conditions described in example 1 step 5. HPLC-MS $t_R$=1.88 min ($UV_{254\ nm}$); mass calculated for formula $C_{23}H_{25}FN_4O_4S$ 472.2, observed LCMS m/z 473.1 (M+H).

Step 3

The compound 2-(3-fluorophenyl)-4-(piperidin-3-yloxy)thieno[2,3-d]pyridazine-7-carboxamide was prepared with the same conditions described in example 1 step 6. HPLC-MS $t_R$=1.33 min ($UV_{254\ nm}$); mass calculated for formula $C_{18}H_{17}FN_4O_2S$ 372.1, observed LCMS m/z 373.1 (M+H).

Example 3

Synthesis of Compound 2-(3-fluorophenyl)-4-(piperidin-3-ylthio)thieno[2,3-d]pyridazine-7-carboxamide was prepared Followed the same procedure described in the example 2, the following compound 2-(3-fluorophenyl)-4-(piperidin-3-ylthio)thieno[2,3-d]pyridazine-7-carboxamide was prepared. HPLC-MS $t_R$=1.35 min ($UV_{254\ nm}$); mass calculated for formula $C_{18}H_{17}FN_4OS_2$ 388.1, observed LCMS m/z 389.0 (M+H).

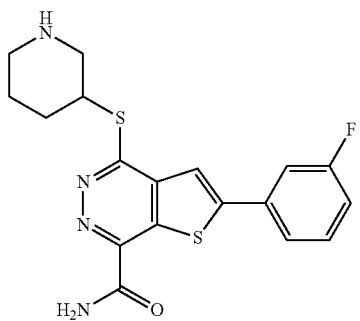 [SMILES: NC(=O)c1nnc(SC2CCCNC2)c2cc(-c3cccc(F)c3)sc12]

Example 4 Synthesis of Compound 2-(3-fluorophenyl)-4-(piperidin-3-ylmethyl)thieno[2,3-d]pyridazine-7-carboxamide

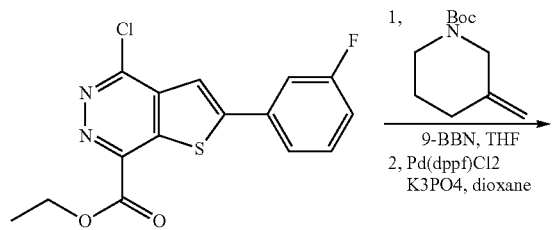

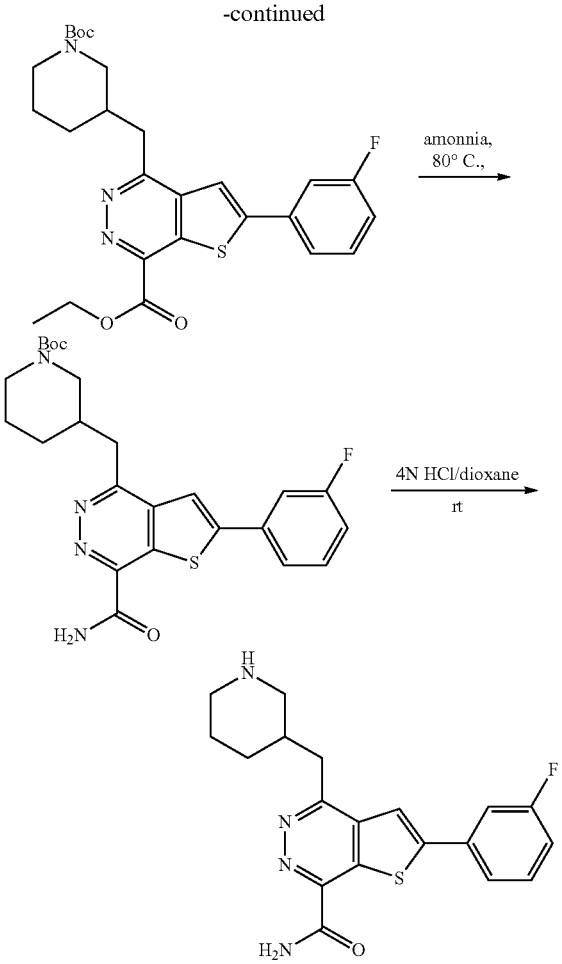

Step 1

Under Ar, the compound tert-butyl 3-methylenepiperidine-1-carboxylate (600 mg, 3.0 mmol) was dissolved in dry THF (15 mmol) and 9-BBN (3.0 mmol) was added dropwise. The resulting mixture was stirred at room temperature for 2 hour. The solution was added to the mixture of the chloro-compound ethyl 4-chloro-2-(3-fluorophenyl)thieno[2,3-d]pyridazine-7-carboxylate (260 mg, 1.0 mmol) was mixed with Pd(dppf)Cl$_2$ (40 mg, 0.05 mmol, $K_3PO_4$ (636 mg, 3.0 mmol), in dioxane (10 mL with 1 ml water) under Ar. The resulting mixture was heated at 90° C. and stirred overnight. After cooled to room temperature, the mixture was diluted with EtOAc (60 mL) and filtered through celite. After concentration, the crude was purified with column (silica gel, 0-30% EtOAc/Hexane) gave the product ethyl 4-((1-(tert-butoxycarbonyl)piperidin-3-yl)methyl)-2-(3-fluorophenyl)thieno[2,3-d]pyridazine-7-carboxylate (266 mg). HPLC-MS $t_R$=2.38 min ($UV_{254\ nm}$); mass calculated for formula $C_{26}H_{30}FN_3O_4S$ 499.2, observed LCMS m/z 500.3 (M+H).

Step 2

The compound tert-butyl 3-((7-carbamoyl-2-(3-fluorophenyl)thieno[2,3-d]pyridazin-4-yl)methyl)piperidine-1-carboxylate was prepared with the same conditions described in example 1 step 5. HPLC-MS $t_R$=1.95 min ($UV_{254\ nm}$); mass calculated for formula $C_{24}H_{27}FN_4O_3S$ 470.2, observed LCMS m/z 471.2 (M+H).

Step 3

The compound 2-(3-fluorophenyl)-4-(piperidin-3-ylmethyl)thieno[2,3-d]pyridazine-7-carboxamide was prepared with the same conditions described in example 1 step 6. HPLC-MS $t_R$=1.39 min (UV$_{254\ nm}$); mass calculated for formula $C_{19}H_{19}FN_4OS$ 370.1, observed LCMS m/z 371.1 (M+H).

Example 4

Similarly, following Scheme 3 described above, the following compounds are synthesized.

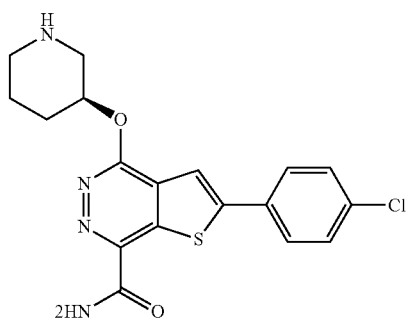

2-(4-Chloro-phenyl)-4-(piperidin-3-yloxy)-thieno[2,3-d]pyridazine-7-carboxylic acid amide

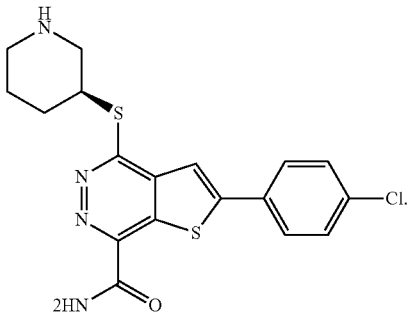

2-(4-Chloro-phenyl)-4-(piperidin-3-ylsulfanyl)-thieno[2,3-d]pyridazine-7-carboxylic acid amide Example 5

Synthesis of Compounds of Formula II

The compounds of the present invention are synthesized as follows: In the presence of a base, a compound of Formula A is treated with dialkyl oxalate, to obtain a compound of formula B:

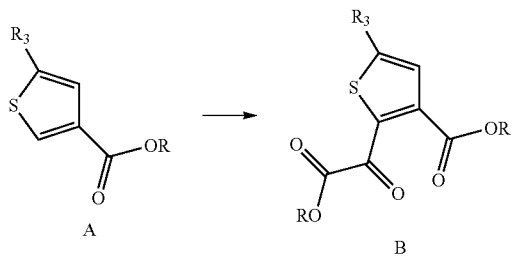

Compound B is treated with hydrazine, to form a compound of Formula C:

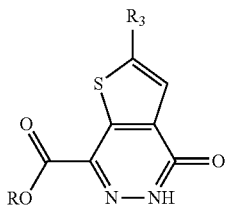

C which is treated with phosphoric trichloride (POCl$_3$), resulting in a compound of Formula D:

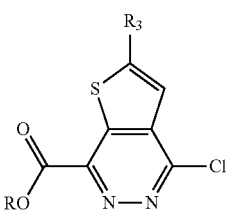

D

Compound D is then reacted with amine NH$_2$R$^1$, to form a compound of Formula E,

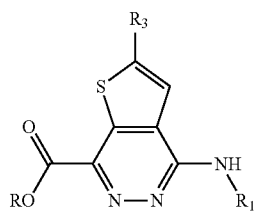

E which is then reacted with another amine, NH$_2$R$^2$, followed by the removal of the protective group on R$^1$, and a treatment with base, resulting in a compound of Formula 1, or a pharmaceutically acceptable salt thereof.

In the above synthesis scheme, R, R$^1$, R$^2$ and R$^3$ are as defined previously. Preferably, R is C$_{1-4}$ alkyl; R$^1$ is a saturated or unsaturated 5- or 6-membered sign containing N, S, or O, or a stereoisomer thereof, R$^2$ is independently H, or a C$_{1-4}$ alkyl; and R$^1$ is a singly or doubly halogen substituted benzyl, which substitution may occur at any position.

Following the above method, the compounds listed below are synthesized:
1. 2-(4-fluorophenyl)-4-(3-piperidineamino)-thieno[2,3-d]pyridazine-7-carboxylic acid amide
2. 2-(4-chlorophenyl)-4-(3-piperidineamino)-thieno[2,3-d]pyridazine-7-carboxylic acid amide
3. 2-(4-bromophenyl)-4-(3-piperidineamino)-thieno[2,3-d]pyridazine-7-carboxylic acid amide
4. 2-(4-fluorophenyl)-4-(3-tetrahydropyran-amino)-thieno[2,3-d]pyridazine-7-carboxylic acid amide
5. 2-(4-chlorophenyl)-4-(3-tetrahydropyran-amino)-thieno[2,3-d]pyridazine-7-carboxylic acid amide
6. 2-(4-bromophenyl)-4-(3-tetrahydropyran-amino)-thieno[2,3-d]pyridazine-7-carboxylic acid amide 7. 2-(4-fluorophenyl)-4-(3-tetrahydrothiopyran-amino)-thieno[2,3-d]pyridazine-7-carboxylic acid amide
8. 2-(4-chlorophenyl)-4-(3-tetrahydrothiopyran-amino)-thieno[2,3-d]pyridazine-7-carboxylic acid amide
9. 2-(4-bromophenyl)-4-(3-tetrahydrothiopyran-amino)-thieno[2,3-d]pyridazine-7-carboxylic acid amide
10. 2-(4-chlorophenyl)-4-(2-piperidine-amino)-thieno[2,3-d]pyridazine-7-carboxylic acid amide
11. 2-(4-chlorophenyl)-4-(2-piperidine-amino)-thieno[2,3-d]pyridazine-7-carboxylic acid amide
12. 2-(4-chlorophenyl)-4-(S-3-piperidine-amino)-thieno[2,3-d]pyridazine-7-carboxylic acid amide
13. 2-(4-chlorophenyl)-4-(R-3-piperidine-amino)-thieno[2,3-d]pyridazine-7-carboxylic acid amide
14. 2-(4-chlorophenyl)-4-(3-piperidine-amino)-thieno[2,3-d]pyridazine-7-N-methyl-carboxylic acid amide
15. 2-(4-chlorophenyl)-4-(3-piperidine-amino)-thieno[2,3-d]pyridazine-7-N,N-dimethyl-carboxylic acid amide
16. 2-(4-chlorophenyl)-4-(3-tetrahydrothiapyran-amino)-thieno[2,3-d]pyridazine-7-N-methyl-carboxylic acid amide
17. 2-(4-chlorophenyl)-4-(3-tetrahydrothiapyran-amino)-thieno[2,3-d]pyridazine-7-N,N-dimethyl-carboxylic acid amide
18. 2-(4-chlorophenyl)-4-(3-tetrahydropyran-amino)-thieno[2,3-d]pyridazine-7-N-methyl-carboxylic acid amide
19. 2-(4-chlorophenyl)-4-(3-tetrahydropyran-amino)-thieno[2,3-d]pyridazine-7-N,N-dimethyl-carboxylic acid amide
20. 2-(4-fluorophenyl)-4-(3-tetrahydropyrrol-amino)-thieno[2,3-d]pyridazine-7-carboxylic acid amide
21. 2-(4-chlorophenyl)-4-(3-tetrahydropyrrol-amino)-thieno[2,3-d]pyridazine-7-carboxylic acid amide
22. 2-(4-bromophenyl)-4-(3-tetrahydropyrrol-amino)-thieno[2,3-d]pyridazine-7-carboxylic acid amide
23. 2-(4-fluorophenyl)-4-(3-tetrahydrofuran-amino)-thieno[2,3-d]pyridazine-7-carboxylic acid amide
24. 2-(4-chlorophenyl)-4-(3-tetrahydrofuran-amino)-thieno[2,3-d]pyridazine-7-carboxylic acid amide
25. 2-(4-bromophenyl)-4-(3-tetrahydrofuran-amino)-thieno[2,3-d]pyridazine-7-carboxylic acid amide
26. 2-(4-fluorophenyl)-4-(3-tetrahydrothieno-amino)-thieno[2,3-d]pyridazine-7-carboxylic acid amide
27. 2-(4-chlorophenyl)-4-(3-tetrahydrothieno-amino)-thieno[2,3-d]pyridazine-7-carboxylic acid amide
28. 2-(4-bromophenyl)-4-(3-tetrahydrothieno-amino)-thieno[2,3-d]pyridazine-7-carboxylic acid amide
29. 2-(4-chlorophenyl)-4-(2-tetrahydropyrrol-amino)-thieno[2,3-d]pyridazine-7-carboxylic acid amide
30. 2-(4-chlorophenyl)-4-(S-3-tetrahydropyrrol-amino)-thieno[2,3-d]pyridazine-7-carboxylic acid amide
31. 2-(4-chlorophenyl)-4-(R-3-tetrahydropyrrol-amino)-thieno[2,3-d]pyridazine-7-carboxylic acid amide
32. 2-(4-chlorophenyl)-4-(3-tetrahydropyrrol-amino)-thieno[2,3-d]pyridazine-7-N-methyl-carboxylic acid amide
33. 2-(4-chlorophenyl)-4-(3-tetrahydropyrrol-amino)-thieno[2,3-d]pyridazine-7-N,N-dimethyl-carboxylic acid amide
34. 2-(4-chlorophenyl)-4-(3-tetrahydrothieno-amino)-thieno[2,3-d]pyridazine-7-N-methyl-carboxylic acid amide
35. 2-(4-chlorophenyl)-4-(3-tetrahydrothieno-amino)-thieno[2,3-d]pyridazine-7-N,N-dimethyl-carboxylic acid amide
36. 2-(4-chlorophenyl)-4-(3-tetrahydrofuran-amino)-thieno[2,3-d]pyridazine-7N-methyl-carboxylic acid amide
37. 2-(4-chlorophenyl)-4-(3-tetrahydrofuran-amino)-thieno[2,3-d]pyridazine-7-N,N-dimethyl-carboxylic acid amide
38. 2-(4-fluorophenyl)-4-(3-pyridin-amino)-thieno[2,3-d]pyridazine-7-carboxylic acid amide
39. 2-(4-chlorophenyl)-4-(3-pyridin-amino)-thieno[2,3-d]pyridazine-7-carboxylic acid amide
40. 2-(4-bromophenyl)-4-(3-pyridin-amino)-thieno[2,3-d]pyridazine-7-carboxylic acid amide
41. 2-(4-fluorophenyl)-4-(3-α-pyran-amino)-thieno[2,3-d]pyridazine-7-carboxylic acid amide
42. 2-(4-chlorophenyl)-4-(3-α-pyran-amino)-thieno[2,3-d]pyridazine-7-carboxylic acid amide
43. 2-(4-bromophenyl)-4-(3-α-pyran-amino)-thieno[2,3-d]pyridazine-7-carboxylic acid amide
44. 2-(4-fluorophenyl)-4-(3-α-thiapyran-amino)-thieno[2,3-d]pyridazine-7-carboxylic acid amide
45. 2-(4-chlorophenyl)-4-(3-α-thiapyran-amino)-thieno[2,3-d]pyridazine-7-carboxylic acid amide
46. 2-(4-bromophenyl)-4-(3-α-thiapyran-amino)-thieno[2,3-d]pyridazine-7-carboxylic acid amide
47. 2-(4-chlorophenyl)-4-(2-pyridin-amino)-thieno[2,3-d]pyridazine-7-carboxylic acid amide
48. 2-(4-chlorophenyl)-4-(4-pyridin-amino)-thieno[2,3-d]pyridazine-7-carboxylic acid amide
49. 2-(4-chlorophenyl)-4-(S-3-pyridin-amino)-thieno[2,3-d]pyridazine-7-carboxylic acid amide
50. 2-(4-chlorophenyl)-4-(R-3-pyridin-amino)-thieno[2,3-d]pyridazine-7-carboxylic acid amide
51. 2-(4-chlorophenyl)-4-(3-pyridin-amino)-thieno[2,3-d]pyridazine-7-N-methyl-carboxylic acid amide
52. 2-(4-chlorophenyl)-4-(3-pyridin-amino)-thieno[2,3-d]pyridazine-7-N,N-dimethyl-carboxylic acid amide
53. 2-(4-chlorophenyl)-4-(3-thiapyran-amino)-thieno[2,3-d]pyridazine-7-N-methyl-carboxylic acid amide
54. 2-(4-chlorophenyl)-4-(3-thiapyran-amino)-thieno[2,3-d]pyridazine-7-N,N-dimethyl-carboxylic acid amide
55. 2-(4-chlorophenyl)-4-(3-pyran-amino)-thieno[2,3-d]pyridazine-7N-methyl-carboxylic acid amide
56. 2-(4-chlorophenyl)-4-(3-pyran-amino)-thieno[2,3-d]pyridazine-7-N,N-dimethyl-carboxylic acid amide
57. 2-(4-fluorophenyl)-4-(3-pyrrol-amino)-thieno[2,3-d]pyridazine-7-carboxylic acid amide
58. 2-(4-chlorophenyl)-4-(3-pyrrol-amino)-thieno[2,3-d]pyridazine-7-carboxylic acid amide
59. 2-(4-bromophenyl)-4-(3-pyrrol-amino)-thieno[2,3-d]pyridazine-7-carboxylic acid amide
60. 2-(4-fluorophenyl)-4-(3-furan-amino)-thieno[2,3-d]pyridazine-7-carboxylic acid amide
61. 2-(4-chlorophenyl)-4-(3-furan-amino)-thieno[2,3-d]pyridazine-7-carboxylic acid amide
62. 2-(4-bromophenyl)-4-(3-furan-amino)-thieno[2,3-d]pyridazine-7-carboxylic acid amide
63. 2-(4-fluorophenyl)-4-(3-thieno-amino)-thieno[2,3-d]pyridazine-7-carboxylic acid amide
64. 2-(4-chlorophenyl)-4-(3-thieno-amino)-thieno[2,3-d]pyridazine-7-carboxylic acid amide
65. 2-(4-bromophenyl)-4-(3-thieno-amino)-thieno[2,3-d]pyridazine-7-carboxylic acid amide
66. 2-(4-chlorophenyl)-4-(2-pyrrol-amino)-thieno[2,3-d]pyridazine-7-carboxylic acid amide
67. 2-(4-chlorophenyl)-4-(S-3-pyrrol-amino)-thieno[2,3-d]pyridazine-7-carboxylic acid amide
68. 2-(4-chlorophenyl)-4-(R-3-pyrrol-amino)-thieno[2,3-d]pyridazine-7-carboxylic acid amide
69. 2-(4-chlorophenyl)-4-(3-pyrrol-amino)-thieno[2,3-d]pyridazine-7-N-methyl-carboxylic acid amide
70. 2-(4-chlorophenyl)-4-(3-pyrrol-amino)-thieno[2,3-d]pyridazine-7-N,N-dimethyl-carboxylic acid amide
71. 2-(4-chlorophenyl)-4-(3-thieno-amino)-thieno[2,3-d]pyridazine-7-N-methyl-carboxylic acid amide 72. 2-(4-chlorophenyl)-4-(3-thieno-amino)-thieno[2,3-d]pyridazine-7-N,N-dimethyl-carboxylic acid amide
73. 2-(4-chlorophenyl)-4-(3-furan-amino)-thieno[2,3-d]pyridazine-7-N-methyl-carboxylic acid amide
74. 2-(4-chlorophenyl)-4-(3-furan-amino)-thieno[2,3-d]pyridazine-7-N,N-dimethyl-carboxylic acid amide
75. 2-(3-fluorophenyl)-4-(3-piperidineamino)-thieno[2,3-d]pyridazine-7-carboxylic acid amide
76. 2-(3-chlorophenyl)-4-(3-piperidineamino)-thieno[2,3-d]pyridazine-7-carboxylic acid amide
77. 2-(3-bromophenyl)-4-(3-piperidineamino)-thieno[2,3-d]pyridazine-7-carboxylic acid amide
78. 2-(3-fluorophenyl)-4-(3-tetrahydropyran-amino)-thieno[2,3-d]pyridazine-7-carboxylic acid amide
79. 2-(3-chlorophenyl)-4-(3-tetrahydropyran-amino)-thieno[2,3-d]pyridazine-7-carboxylic acid amide
80. 2-(3-bromophenyl)-4-(3-tetrahydropyran-amino)-thieno[2,3-d]pyridazine-7-carboxylic acid amide
81. 2-(3-fluorophenyl)-4-(3-tetrahydrothiapyran-amino)-thieno[2,3-d]pyridazine-7-carboxylic acid amide
82. 2-(3-chlorophenyl)-4-(3-tetrahydrothiapyran-amino)-thieno[2,3-d]pyridazine-7-carboxylic acid amide
83. 2-(3-bromophenyl)-4-(3-tetrahydrothiapyran-amino)-thieno[2,3-d]pyridazine-7-carboxylic acid amide
84. 2-(3-chlorophenyl)-4-(2-piperidine-amino)-thieno[2,3-d]pyridazine-7-carboxylic acid amide
85. 2-(3-chlorophenyl)-4-(2-piperidine-amino)-thieno[2,3-d]pyridazine-7-carboxylic acid amide
86. 2-(3-chlorophenyl)-4-(S-3-piperidine-amino)-thieno[2,3-d]pyridazine-7-carboxylic acid amide
87. 2-(3-chlorophenyl)-4-(R-3-piperidine-amino)-thieno[2,3-d]pyridazine-7-carboxylic acid amide
88. 2-(3-chlorophenyl)-4-(3-piperidine-amino)-thieno[2,3-d]pyridazine-7-N-methyl-carboxylic acid amide
89. 2-(3-chlorophenyl)-4-(3-piperidine-amino)-thieno[2,3-d]pyridazine-7-N,N-dimethyl-carboxylic acid amide
90. 2-(3-chlorophenyl)-4-(3-tetrahydrothiapyran-amino)-thieno[2,3-d]pyridazine-7-N-methyl-carboxylic acid amide
91. 2-(3-chlorophenyl)-4-(3-tetrahydrothiapyran-amino)-thieno[2,3-d]pyridazine-7-N,N-dimethyl-carboxylic acid amide
92. 2-(3-chlorophenyl)-4-(3-tetrahydropyran-amino)-thieno[2,3-d]pyridazine-7-N-methyl-carboxylic acid amide
93. 2-(3-chlorophenyl)-4-(3-tetrahydropyran-amino)-thieno[2,3-d]pyridazine-7-N,N-dimethyl-carboxylic acid amide
94. 2-(3-fluorophenyl)-4-(3-tetrahydropyrrol-amino)-thieno[2,3-d]pyridazine-7-carboxylic acid amide
95. 2-(3-chlorophenyl)-4-(3-tetrahydropyrrol-amino)-thieno[2,3-d]pyridazine-7-carboxylic acid amide
96. 2-(3-bromophenyl)-4-(3-tetrahydropyrrol-amino)-thieno[2,3-d]pyridazine-7-carboxylic acid amide
97. 2-(3-fluorophenyl)-4-(3-tetrahydrofuran-amino)-thieno[2,3-d]pyridazine-7-carboxylic acid amide
98. 2-(3-chlorophenyl)-4-(3-tetrahydrofuran-amino)-thieno[2,3-d]pyridazine-7-carboxylic acid amide
99. 2-(3-bromophenyl)-4-(3-tetrahydrofuran-amino)-thieno[2,3-d]pyridazine-7-carboxylic acid amide
100. 2-(3-fluorophenyl)-4-(3-tetrahydrothieno-amino)-thieno[2,3-d]pyridazine-7-carboxylic acid amide
101. 2-(3-chlorophenyl)-4-(3-tetrahydrothieno-amino)-thieno[2,3-d]pyridazine-7-carboxylic acid amide
102. 2-(3-bromophenyl)-4-(3-tetrahydrothieno-amino)-thieno[2,3-d]pyridazine-7-carboxylic acid amide
103. 2-(3-chlorophenyl)-4-(2-tetrahydropyrrol-amino)-thieno[2,3-d]pyridazine-7-carboxylic acid amide
104. 2-(3-chlorophenyl)-4-(S-3-tetrahydropyrrol-amino)-thieno[2,3-d]pyridazine-7-carboxylic acid amide
105. 2-(3-chlorophenyl)-4-(R-3-tetrahydropyrrol-amino)-thieno[2,3-d]pyridazine-7-carboxylic acid amide
106. 2-(3-chlorophenyl)-4-(3-tetrahydropyrrol-amino)-thieno[2,3-d]pyridazine-7-N-methyl-carboxylic acid amide
107. 2-(3-chlorophenyl)-4-(3-tetrahydropyrrol-amino)-thieno[2,3-d]pyridazine-7-N,N-dimethyl-carboxylic acid amide
108. 2-(3-chlorophenyl)-4-(3-tetrahydrothieno-amino)-thieno[2,3-d]pyridazine-7-N-methyl-carboxylic acid amide
109. 2-(3-chlorophenyl)-4-(3-tetrahydrothieno-amino)-thieno[2,3-d]pyridazine-7-N,N-dimethyl-carboxylic acid amide
110. 2-(3-chlorophenyl)-4-(3-tetrahydrofuran-amino)-thieno[2,3-d]pyridazine-7-N-methyl-carboxylic acid amide
111. 2-(3-chlorophenyl)-4-(3-tetrahydrofuran-amino)-thieno[2,3-d]pyridazine-7-N,N-dimethyl-carboxylic acid amide
112. 2-(3-fluorophenyl)-4-(3-pyridin-amino)-thieno[2,3-d]pyridazine-7-carboxylic acid amide
113. 2-(3-chlorophenyl)-4-(3-pyridin-amino)-thieno[2,3-d]pyridazine-7-carboxylic acid amide
114. 2-(3-bromophenyl)-4-(3-pyridin-amino)-thieno[2,3-d]pyridazine-7-carboxylic acid amide
115. 2-(3-fluorophenyl)-4-(3-α-pyran-amino)-thieno[2,3-d]pyridazine-7-carboxylic acid amide
116. 2-(3-chlorophenyl)-4-(3-α-pyran-amino)-thieno[2,3-d]pyridazine-7-carboxylic acid amide
117. 2-(3-bromophenyl)-4-(3-α-pyran-amino)-thieno[2,3-d]pyridazine-7-carboxylic acid amide
118. 2-(3-fluorophenyl)-4-(3-α-thiapyran-amino)-thieno[2,3-d]pyridazine-7-carboxylic acid amide
119. 2-(3-chlorophenyl)-4-(3-α-thiapyran-amino)-thieno[2,3-d]pyridazine-7-carboxylic acid amide
120. 2-(3-bromophenyl)-4-(3-α-thiapyran-amino)-thieno[2,3-d]pyridazine-7-carboxylic acid amide
121. 2-(3-chlorophenyl)-4-(2-pyridin-amino)-thieno[2,3-d]pyridazine-7-carboxylic acid amide
122. 2-(3-chlorophenyl)-4-(4-pyridin-amino)-thieno[2,3-d]pyridazine-7-carboxylic acid amide
123. 2-(3-chlorophenyl)-4-(S-3-pyridin-amino)-thieno[2,3-d]pyridazine-7-carboxylic acid amide
124. 2-(3-chlorophenyl)-4-(R-3-pyridin-amino)-thieno[2,3-d]pyridazine-7-carboxylic acid amide
125. 2-(3-chlorophenyl)-4-(3-pyridin-amino)-thieno[2,3-d]pyridazine-7-N-methyl-carboxylic acid amide
126. 2-(3-chlorophenyl)-4-(3-pyridin-amino)-thieno[2,3-d]pyridazine-7-N,N-dimethyl-carboxylic acid amide
127. 2-(3-chlorophenyl)-4-(3-thiapyran-amino)-thieno[2,3-d]pyridazine-7-N-methyl-carboxylic acid amide
128. 2-(3-chlorophenyl)-4-(3-thiapyran-amino)-thieno[2,3-d]pyridazine-7-N,N-dimethyl-carboxylic acid amide
129. 2-(3-chlorophenyl)-4-(3-pyran-amino)-thieno[2,3-d]pyridazine-7-N-methyl-carboxylic acid amide
130. 2-(3-chlorophenyl)-4-(3-pyran-amino)-thieno[2,3-d]pyridazine-7-N,N-dimethyl-carboxylic acid amide
131. 2-(3-fluorophenyl)-4-(3-pyrrol-amino)-thieno[2,3-d]pyridazine-7-carboxylic acid amide
132. 2-(3-chlorophenyl)-4-(3-pyrrol-amino)-thieno[2,3-d]pyridazine-7-carboxylic acid amide
133. 2-(3-bromophenyl)-4-(3-pyrrol-amino)-thieno[2,3-d]pyridazine-7-carboxylic acid amide 134. 2-(3-fluorophenyl)-4-(3-furan-amino)-thieno[2,3-d]pyridazine-7-carboxylic acid amide
135. 2-(3-chlorophenyl)-4-(3-furan-amino)-thieno[2,3-d]pyridazine-7-carboxylic acid amide
136. 2-(3-bromophenyl)-4-(3-furan-amino)-thieno[2,3-d]pyridazine-7-carboxylic acid amide
137. 2-(3-fluorophenyl)-4-(3-thieno-amino)-thieno[2,3-d]pyridazine-7-carboxylic acid amide
138. 2-(3-chlorophenyl)-4-(3-thieno-amino)-thieno[2,3-d]pyridazine-7-carboxylic acid amide
139. 2-(3-bromophenyl)-4-(3-thieno-amino)-thieno[2,3-d]pyridazine-7-carboxylic acid amide
140. 2-(3-chlorophenyl)-4-(2-pyrrol-amino)-thieno[2,3-d]pyridazine-7-carboxylic acid amide
141. 2-(3-chlorophenyl)-4-(S-3-pyrrol-amino)-thieno[2,3-d]pyridazine-7-carboxylic acid amide
142. 2-(3-chlorophenyl)-4-(R-3-pyrrol-amino)-thieno[2,3-d]pyridazine-7-carboxylic acid amide
143. 2-(3-chlorophenyl)-4-(3-pyrrol-amino)-thieno[2,3-d]pyridazine-7-N-methyl-carboxylic acid amide
144. 2-(3-chlorophenyl)-4-(3-pyrrol-amino)-thieno[2,3-d]pyridazine-7-N,N-dimethyl-carboxylic acid amide
145. 2-(3-chlorophenyl)-4-(3-thieno-amino)-thieno[2,3-d]pyridazine-7-N-methyl-carboxylic acid amide
146. 2-(3-chlorophenyl)-4-(3-thieno-amino)-thieno[2,3-d]pyridazine-7-N,N-dimethyl-carboxylic acid amide
147. 2-(3-chlorophenyl)-4-(3-furan-amino)-thieno[2,3-d]pyridazine-7-N-methyl-carboxylic acid amide, and
148. 2-(3-chlorophenyl)-4-(3-furan-amino)-thieno[2,3-d]pyridazine-7-N,N-dimethyl-carboxylic acid amide.

Example 6

Formulations

Pharmaceutical preparations for delivery by various routes are formulated as shown in the following. "Active ingredient" or "Active compound" as used in the following means one or more of the compounds of Formula I.

1. Parenteral injection. Formulation: Active ingredient, 50 g; Sodium chloride, 2250 g; Water for injection add to 250,000 ml, to make 1,000 bottles.

Preparation: The active ingredient is dissolved in a portion of water for injection; a sufficient quantity of sodium chloride is then added with stirring to make the solution isotonic. Its pH is adjusted to 4.0 to 5.0. Activated carbon (250 g) is added to for 30 min and then removed using a filter rod. The mixture is then bottled in 250 ml/after filtration with Titanium Rod until the solution is clear, which is then sterilized in a 115□ water bath for 30 min.

2. Pellet. Formulation: Active ingredient, 50 g; Starch, 160 g; Hydroxypropyl cellulose, 39 g; Polyvidone K30, q.s.; sodium carboxymethyl starch, 10.4 g; magnesium stearate, 1.3 g; for making 1000 tablets.

Preparation: Active ingredient, starch and Hydroxypropyl cellulose are placed in the hopper of a fluid bed granulator and warmed to 38-60 □. Polyvidone K30 water solution is nebulized to granulate the mixture. The mixture is then dried at 55-60□ for 10 min, mixed with sodium carboxymethyl starch and magnesium stearate to tabletting.

3. Capsule. Formulation: Active ingredient, 50 g; lactose, 194.4 g; sodium carboxymethylstarch, 7.8 g; silicon dioxide, 5.2 g; magnesium stearate, 2.6 g.

Preparation: Mix active ingredient, Lactose, sodium carboxymethylstarch and silicon dioxide in the mixer for 1 h and then added magnesium stearate for another 10 min before filled in gelatin plastic shell.

Example 7

Toxicity, In Vitro and In Vivo Effectiveness Tests

Some of the above compounds are tested in vitro or in vivo for their anti-cancer or anti-tumor activities, as well as cellular toxicity tests using SRB and MTT methods. The in vitro anti-cancer effects on human cancer HT-29 and mouse lung cancer cell 3LL are summarized in Table 1, and the effects on treating transplanted human colon cancer HT-99 on nude mice are summarized in Table 2.

TABLE 1

In vitro anti-cancer cell activities $IC_{50}$ (μM)

| Compound No. | Human colon cancer HT-29 | Mouse Lung Cancer (3LL) |
|---|---|---|
| 1 | 1.58 | 1.88 |

TABLE 2

Effects on Human colon cancer HT-99 Transplanted Nude Mice

| Compound No. | Dosage (mg/kg) | Admin. Route | Do/dn | TC (%) |
|---|---|---|---|---|
| GCT + 1 | 20 + 15 | ip + iv | 6/6 | 30 |
| GCT | 20 | ip | 6/6 | 45 |
| Negative Control | solution | ip | 06/05/09 | |

Notes:
ip = intra-peritoneal injection
iv: intravenous injection;
GCT = gemcitabine The data above show that the compounds of the present invention have anti-tumor effects, and can also enhance the anti-tumor effects of other compounds such as GCT, CPT-11, ADR.

Example 8

In Vitro Anticancer Effects of XC608

Materials and Methods

Cell lines: human low differentiation stomach cancer BGC-823, human liver cancer QGY-7701, mouse lung cancer 3LL.

DMEM cell culture medium (GIBCO BRL), supplemented with 10% bovine fetal serum, L-glutamine, and antibiotics 0.25% Trypsin solution (Invitrogen)

MTT Solution: made using phosphate buffer solution to 5 mg/ml.

Dissolution solution: SDS 10 g, isobutanol 5 ml, and concentrated sulfuric acid 0.12 ml, added into 100 ml double distilled water.

Test compound and method of preparation. The compound used for this test is XC608, which is a whitish powder and has the following formula:

XC608

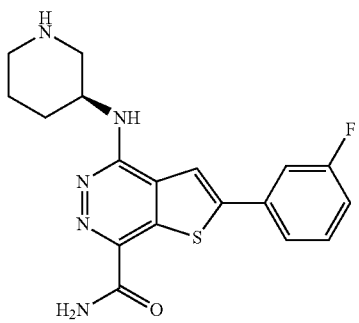

Control: XC302, another anticancer compound that is undergoing clinical trial.

Experimental Details: The cyto-toxicity of XC608 is measured using the MTT method. Specifically: (1) cell culture: (i) frozen cells are removed from liquid nitrogen, rapidly thawed in 37° C. water bath; added to 6 ml DMEM culture medium in a 10 ml centrifuge tubes under sterile conditions, centrifuged at 1000 rpm for 5 min., with the supernatant removed. To the sediment is added 5-6 ml of DMEM medium, and re-suspended and cultured overnight at 37° C. (ii) The cells are centrifuged, washed twice with PBS, and treated with 3-4 drops of trypsin solution for about 3 minute at 37° C. and monitored under microscope to ensure that all cells are separated from the culture tube walls, and re-suspended in additional DMEM medium. The cells are separated into additional cultural vessels, and the above process repeated to ensure that the wall-adhered cells do not become overly dense and suspended cells remain in log-growth state. (2) Test compound preparation: XC608 and XC302 are dissolved in PBS and serial diluted to 1000, 100, 10, 1, 0.1 and 0.01 µg/ml. (3) The prepared test compound solution is added to the holes of a 96-hole culture plate, 10 µl/hole, with two holes per concentration point, and 10 µl PBS as control. (4) Prepare a suspension of log phase cell in a DMEM medium containing 10% new born bovine serum with a cell concentration of $2 \times 10^5$/ml. (5) add 90 µl cell suspension to each of the holes containing the test compound or control. (6) culture the cells at 37° C. under 5% CO2 for 48 hours. (7) Add 20 µl of 5 mg/ml MTT solution, and continue to culture for 3-4 hours. (8) Add 20 µl dissolution solution, and culture overnight. This ensures the formazan crystals are completely dissolved. (9) measure $OD_{570}$. (10) calculate relative cell survival rate by the formula: Relative cell survival rate=(treatment group OD−Background OD)/(PBS Control Group OD-Background OD)×100%.

Results: The results are shown in Table 3 below:

TABLE 3

Inhibitive effects of X608 on cancer cell multiplication

| Cell lines | IC$_{50}$ (µg/ml) | |
| --- | --- | --- |
| | XC608 | XC302 |
| BGC-823 | 7.11 | 4.77 |
| QGY-7701 | 5.14 | 6.69 |
| 3LL | 1.05 | 2.96 |

Example 9

XC608 combined with Gemcitabine more effectively inhibits human ovarian cancer in nude mice Objectives: Using the nude mice human ovarian cancer model (BALB/c-nu) to test the effect of XC608, XC608-Cl, AZD7762 combined with Gemcitabine in cancer treatment.

Experimental Details

1. Test compound and method of preparation The compound used for this test is XC608, shown above, and XC608-Cl is the chloride salt of XC608, 090208-1, also a whitish powder. AZD7762 is a yellow powder.

All of the above are dissolved in 5% glucose injectable solution and diluted to suitable concentrations. Control: Gemcitabine is obtained from Jiangsu Haosen Pharmaceuticals Co., Ltd., also dissolved to suitable concentration in saline solution.

Animals and Cancer Cell Lines: Test animals: 30 nude mice BALB/c-nu, female, bw 18-20 g, supplied by B&K Universal Group Limited, Shanghai, China. Cancer cell lines: the human ovarian cell line is from a commercial source, transplanted onto nude mice, which were maintained by Shanghai Pharmaceutical Industry Research Institute.

Test Methods: The tumors from the ovarian cancer carrying nude mice is isolated and cut into 1-mm$^3$ pieces, which are then implanted subcutaneously to the test nude mice. After 10 days, the tumors grow to a size of about 0.1 cm$^3$. The test mice are randomly divided into 5 groups of six animals.

Treatment Groups: Gemcitabine 25 mg/kg+XC608-F 50 mg/kg, Gemcitabine 25 mg/kg+AZD7762 10 mg/kg, and control.

Starting from 11 days after tumor implant, the animals are administered the test compounds i.v. The animals are weighed every two days, and the tumor volume is measured. After 24 days from the beginning of test compound administration, the animals are killed and the tumors are isolated and weighed.

The tumor volume (TV) is measured and calculated.

Relative Tumor volume (RTV) is Vt/V0, wherein Vt is the tumor volume at the measurement time, while V0 is the tumor volume when drug administration was started.

A compound's antitumor activity is measured by the RTV growth rate, T/C (%), which is calculated as: T/C=Treatment RTC/Control Group RTC×100%.

If TC (%) is more than 60, then the treatment is considered to have no effect. Only when the TC is less than 60, an the difference is statistically significant would the treatment be considered to be effective.

Another measurement is rate of tumor inhibition, which is IR (%)=(control group tumor weight−treatment group tumor weight)/control group tumor weight×100%.

Results: The results are summarized in the two tables below:

TABLE 4-1

Effects of XC608, and XC608-Cl (i.v.) combined with Gemcitabine in treating human ovarian cancer transplanted nude mice (body weight)

| Group | Dosage (mg/kg) | Animal Count d0 | Animal Count dn | Body Weight (with tumor) (g) d0 | Body Weight (with tumor) (g) dn | Body Weight (no tumor) (g) Dn |
|---|---|---|---|---|---|---|
| Gemcitabine | 25 | 6 | 6 | 21.38 | 25.50 | 22.65 |
| G + XC608Cl | 25 + 50 | 6 | 6 | 20.50 | 23.57 | 21.40 |
| G + 608 | 25 + 50 | 6 | 6 | 20.70 | 23.48 | 22.03 |
| G + AZD | 25 + 10 | 6 | 6 | 20.98 | 23.57 | 22.03 |
| Control | | 6 | 6 | 20.63 | 25.88 | 22.33 |

TABLE 4-2

Effects of XC608, and XC608-Cl (i.v.) combined with Gemcitabine in treating human ovarian cancer transplanted nude mice (tumor volume and weight)

| Group | TV mm$^3$ d0 | TV mm$^3$ Dn | RTV dn | T/C % Dn | Tumor Weight g dn | Tumor RI % dn | Tumor RI/ Gemcitabine |
|---|---|---|---|---|---|---|---|
| Gemcitabine | 143.67 ± 44.38 | 1734.05 ± 586.49 | 12.07 | 82.27 | 2.85 | 19.72 | |
| G + XC608Cl | 140.95 ± 47.93 | 1173.39 ± 511.44 | 8.32 | 56.75* | 2.17 | 38.97 | 23.98 |
| G + 608 | 145.00 ± 50.38 | 969.22 ± 330.78 | 6.68 | 45.56* | 1.45 | 59.15 | 49.12 |
| G + AZD | 144.94 ± 68.50 | 980.01 ± 272.98 | 6.76 | 46.09** | 1.53 | 56.81 | 46.20 |
| Control | 147.72 ± 63.19 | 2167.02 ± 545.18 | 14.67 | 100.00 | 3.55 | | |

Note:
*p < 0.05;
**p < 0.01;
i.v. = intravenous injection

A graphical depiction of the above results in shown in FIG. 1.

Example 10

Anti-Cancer Effects of XC608 and its Mechanism

I. Summary

The experiments below examined the action mechanism and sensitizing effect of XC608 on cytotoxic antitumor drugs, as well as its therapeutic effects when combined with 5-fluorouracil (5-Fu) and adriamycin (ADR) on nude mice with transplanted human colon cancer and breast cancer.

Action Mechanism of XC608

XC608 clearly inhibits the activities of Chk1 and Chk2, but has not apparent effect on c-met, HER2, or EGFR; it eliminates cdc2 phosphorylation induced by topoisomerase I, drives cells with DNA damages to continue to enter cell cycle; and clearly enhances the reaction of the cells to drugs that cause DNA damages. These results, taken together, demonstrate that XC608 is a specific Chk1 inhibitor, and sensitizing other anticancer drugs by inhibiting the DNA repair process.

2. Effects of XC608 on Sensitizing Cytotoxic Anti-Cancer Drugs at the Cellular Level The effects of XC608 and AZD7762 on a number of cytotoxic antitumor drugs are evaluated using cell cultures. The cytotoxic antitumor drugs include cisplatin (DDP), paclitaxel, pemetrexed, 5-fluorouracil (5-fu), vinorelbine, oxaliplatin, and gemcitabine are studied. The results show that XC608 has strong sensitizing effects on gemcitabine, DDP, 5-fu and pemetrexed, with that on gemcitabine being the highest, reaching more than 20 times.

3. Animal Tests Showing the Effects of XC608 on Sensitizing Cytotoxic Anti-Cancer Drugs Nude mice transplanted with human colon cancer HT-29 and SW-620 and breast cancer MDA-MB-231 are tested using XC608 alone and in combination with ADR and 5-fu.

Results show that XC608 has significant sensitizing effects on the treatment effects of ADR and 5-fu on HT-29 and SW-620.

4. Conclusion

XC608 is a specific Chk1 inhibitor; it sensitizes the cancer cells to enhance the effects of other cytotoxic anticancer drugs by inhibiting DNA damage repair. Such sensitizing effects of XC608 is strongly correlated with the types of cytotoxic anticancer drugs as well as the types of cancer cell lines.

II. Action Mechanism of XC608

1. Summary

The effects of XC608 on the activity of protein kinases Chk1, Chk2 and c-met, and on cells entering cell cycle after drug-induced DNA damages and cellular reactions to DNA damages are studied. XC608 strongly inhibits the activities of Chk-1 and Chk-2, reduces topoisomerase I induced cdc-2 phosphorylation, and drives cells to continue to enter cell cycle. At the same time, XC608 clearly increased cellular susceptibility to DNA damages. These results show that XC608 inhibits DNA damage repair.

2. Materials and Methods

XC608 and AZD-7762 are whitish powder, with a lot number of 090309-2 and 081107, respectively. They well dissolved in DMSO into 10 mM stock solution.

The K-LISA™ Chk-1/Chk2 Activity Kit was supplied by Calibiochem (Cat. No. CBA020). Chk1 and Chk2 are from Upstate Biotechnology, Inc., and C-Met, HER2, EGFR are from Sigma. The Chk Peptide (KKKVSRSGLYR-SPSMPENLNRPR) (SEQ ID NO: 1) is from Cell Signaling, Inc., (Beverly, Mass., USA), and is stored at −70° C.

The cell line HT29 is purchased from ATCC, and cultured at 37° C. with 5% $CO_2$ on Mycoy's SA medium (GIBCO, Grand Island, N.Y., USA), which contains 10% bovine serum, L-glutamine, penicillin (100 IU/ml) and streptomycin (100 μg/ml).

Kinase activity measurements: Enzyme, sample, Chk peptide, 5 μm ATP, and reaction buffer are added to the holes of biotinylated reaction plates. After the reaction is terminated with a stop buffer, the contents are discarded, replaced with 100 μl/hole of serine kinase antibody, to detect phosphorylation, and HRP-labeled goat-anti-rabbit IgG is added and incubated at room temperature for 1 hour. TMB reaction is conducted to determine substrate phosphorylation, with proper controls. OD450 is measured using VERSAmax (Sunnyvale, Calif., USA). The rate of inhibition is calculated as the follows: Rate of Inhibition (I)=(reaction hole OD Value−OD value of Enzyme-free control)/(OD value of negative control−OD value of enzyme-free control)×100%.

4. Results 4.1 Effects of XC608 on Protein Kinases

These results are shown in Table 5, which shows that XC608 has strong inhibitive effect on protein kinases.

TABLE 5

Effects of XC608 on Protein Kinase Activities

| Drugs | Inhibition (%) (Mean ± SD) | | | | |
|---|---|---|---|---|---|
| | Chk1 | Chk2 | c-Met | HER2 | EGFR |
| XC608 (1 μM) | 85 ± 11.1 | 90 ± 13.2 | 15.9± | 10.2 ± 1.3 | 15.9 ± 5.3 |
| AZD7762 (100 nM) | 80.6 ± 11.3 | 99 ± 0 | / | / | / |

III. Effects of XC608 on Sensitizing Cancers Cells to Cytotoxic Anti-Cancer Drugs 1. Summary The effects of XC608 and AZD7762 on a number of cytotoxic antitumor drugs are evaluated. The cytotoxic antitumor drugs include cisplatin (DDP), paclitaxel, pemetrexed, 5-fluorouracil (5-fu), vinorelbine, oxaliplatin, and gemcitabine are studied. The results show that XC608 has strong sensitizing effects on gemcitabine, DDP, 5-fu and pemetrexed, with that on gemcitabine being the highest, reaching more than 20 times.

2. Objectives

The effects of XC608 in sensitizing the cells for a number of cytotoxic antitumor drugs are evaluated, and compared with that of a known sensitizer AZD7762.

3. Materials and Methods 3.1 Test Compounds: XC608 and AZD-7762 are whitish powder, with a lot number of 090309-2 and 081107, respectively.

3.2 Cell Lines: HT-29 Cell line (from ATCC).

3.3 Equipment/Devices: McCoy's 5a, from Gibco BRL; bovine fetal serum from JRH; McCoy's 5a, from Gibco BRL: bovine fetal serum, from JRH Biosciences, Australia, SPECTRA MAX 190 microplate spectrophotometer, from Molecular Device; SRB from Sigma.

4. Test Protocol: The effects of the compounds on cancer cell multiplication was measured using Sulforhodamine B (SRB). Specifically, log phase cells are inoculated into the holes of 96-hole culture plates, allowed to grow using the wall-adhesion procedure at 37° C. under 5% $CO_2$. The test compound at 9 different concentrations were added, each concentration in duplicate, with appropriate saline water and cell-less controls. The cells are cultured for a further 72 hours, and fixed with TCA, and SRB is added for staining, and washed, and air-dried. After adding the Tris solution, the OD value was measured at 510 nm using a Spectra Max 190. The rate of inhibition is calculated according to the formula below: Rate of Inhibition=$(OD_{control}-OD_{drug})/OD_{control}\times$100%.

The $IC_{50}$ is calculated based on the above ratios.

5. Results The sensitizing effects of XCCS650(S) and AZD7762 are shown in Table 6. Consistent with prior results, XC608 has strong sensitizing effects on gemcitabine, DDP, 5-fu and pemetrexed, with that on gemcitabine being the highest, reaching more than 20 times.

TABLE 6

Sensitizing Effects of XC608 on Cytocotix Antitumor Drugs

| | $IC_{50}$ (μM) | | | |
|---|---|---|---|---|
| Drugs | Drug alone | +1 μM XC608 | +10 nM AZD7762 | +100 nM AZD7762 |
| DDP | 7.7 | 1.3 | 5.2 (1.6) | 1.3 |
| Paclitaxel | 0.003 | 0.002 (1.0) | 0.003 (1.0) | 0.005 (1.1) |
| 5-Fu | 1.1 | 0.2 | 1.0 (1.1) | 0.3 |
| oxaliplatin | 1.6 | 1.3 (1.2) | 2.5 (0.7) | 1.1 (1.4) |
| Gemcitabine | 0.07 | 0.003 | 0.03 (2.0) | 0.005 |

Conclusion: XC-608 is effective in sensitizing the cancer cells for cytotoxic anti-cancer drugs DDP, 5-Fu, oxaliplatin, and Gemcitabine.

Example 11

Anti-Cancer Effects of XC620 and its Mechanism

A compound identical to XC608 except where in Formula I Y=O is synthesized and designated XC620. The action mechanism and sensitizing effect of XC620 on cytotoxic antitumor drugs, as well as its therapeutic effects when combined with 5-fluorouracil (5-Fu) and adriamycin (ADR) on nude mice with transplanted human colon cancer and breast cancer are also tested, following the protocols described above. The results show that XC620 also clearly inhibits the activities of Chk1 and Chk2, and is a specific Chk1 inhibitor, and sensitizing other anticancer drugs by inhibiting the DNA repair process.

The effects of XC620 on sensitizing cytotoxic anti-cancer drugs at the cellular level are comparable to XC608. It also has similar effect, though not as effective, on sensitizing tumor cell lines for cytotoxic antitumor drugs include cisplatin (DDP), paclitaxel, pemetrexed, 5-fluorouracil (5-fu), vinorelbine, oxaliplatin, and gemcitabine are studied.

Thus, XC620 is a also specific Chk1 inhibitor; it sensitizes the cancer cells to enhance the effects of other cytotoxic anticancer drugs by inhibiting DNA damage repair.

Example 12

Anti-Cancer Effects of XC655 and its Mechanism

A compound identical to XC608 except where in Formula I Y=S is synthesized and designated XC620. The action mechanism and sensitizing effect of XC655 on cytotoxic antitumor drugs, as well as its therapeutic effects when combined with 5-fluorouracil (5-Fu) and adriamycin (ADR)

on nude mice with transplanted human colon cancer and breast cancer are also tested, following the protocols described above. The results show that XC655 also clearly inhibits the activities of Chk1 and Chk2, and is a specific Chk1 inhibitor, and sensitizing other anticancer drugs by inhibiting the DNA repair process.

The effects of XC655 on sensitizing cytotoxic anti-cancer drugs at the cellular level are comparable to XC608. It also has similar effect, though not as effective, on sensitizing tumor cell lines for cytotoxic antitumor drugs include cisplatin (DDP), paclitaxel, pemetrexed, 5-fluorouracil (5-fu), vinorelbine, oxaliplatin, and gemcitabine are studied.

XC650 is therefore also specific Chk1 inhibitor; it sensitizes the cancer cells to enhance the effects of other cytotoxic anticancer drugs by inhibiting DNA damage repair.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

What is claimed is:

1. A compound of formula I:

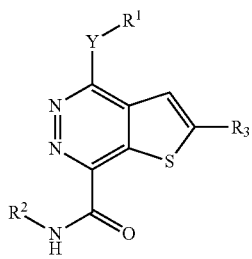

(I)

wherein
Y=O, or S,
$R^1$=selected from following groups:

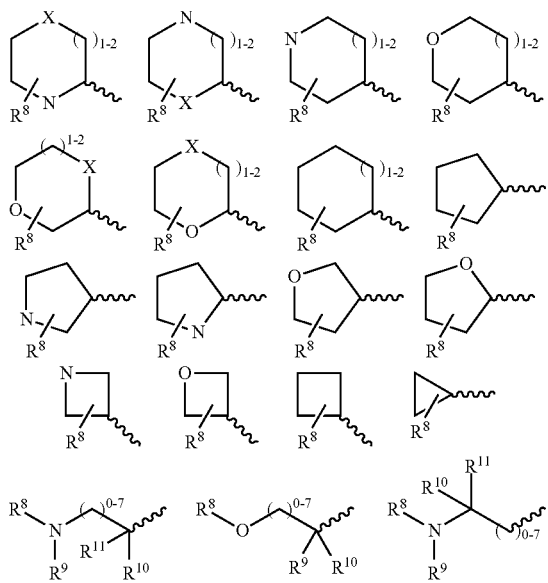

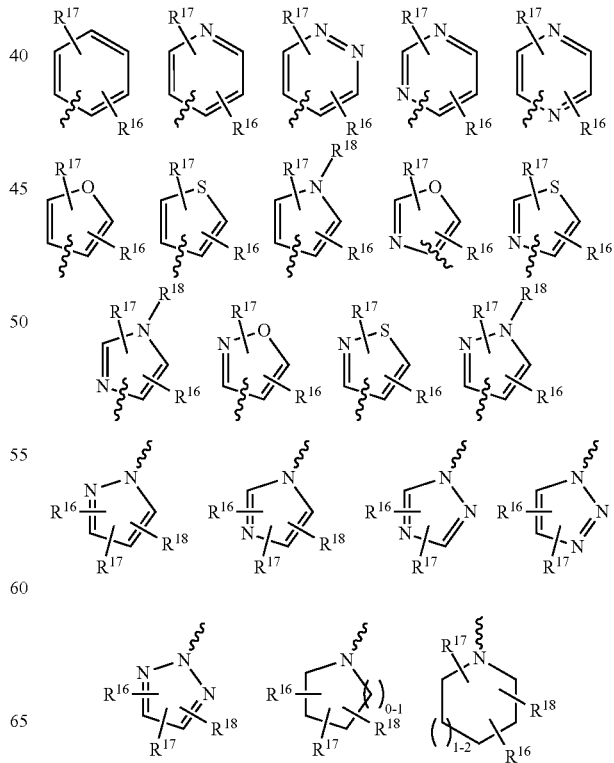

wherein X =$CH_2$, NH, S, or O,
$R^8$=—H, —$NH_2$, —OH, —N($R^4$, $R^5$), —C($R^4R^5$)$_{1-7}$ $NR^6R^7$, —C($R^4R^5$)$_{1-7}$$OR^6$, or —N($R^4$)$NR^5R^6$, wherein $R^4$, $R^5$, $R^6$, $R^7$=H, alkyls ($C_1$-$C_6$), cycloalkyls ($C_3$-$C_8$) with or without nuclear heteroatoms such as O, S, and N, aryls (either unsubstituted or substituted aromatics), or heteroaromatics (either unsubstituted or substituted heteroaromatics), $R^9$, $R^{10}$, $R^{11}$, $R^{12}$, and $R^{13}$=H, alkyls ($C_1$-$C_6$), cycloalkyls ($C_3$-$C_8$) with or without nuclear heteroatoms such as O, S or N; aryls (either unsubstituted and substituted aromatics), or heteroaromatics (either unsubstituted or substituted heteroaromatics), $R^2$, is selected from a group consisting of H, OH, $NH_2$, $OR^{14}$, $NR^{14}R^{15}$, alkyl, aryl, heteroaryl, cycloalkyl, arylalkyl, heterocyclyl, heterocyclylalkyl, alkenyl, and alkynyl,
wherein $R^{14}$, $R^{15}$=H, alkyls ($C_1$-$C_6$), cycloalkyls ($C_3$-$C_8$) with or without nuclear heteroatoms such as O, S, N, aryls (either unsubstituted or substituted aromatics), or heteroaromatics (either unsubstituted or substituted heteroaromatics), and $R^3$ is selected from a group consisting of H, alkyl, aryl, heteroaryl, cycloalkyl, arylalkyl, heterocyclyl, heterocyclylalkyl, alkenyl, and alkynyl, Specifically $R^3$ is selected from the following groups:

wherein $R^{16}$, $R^{17}$, and $R^{18}$ are selected from following groups: H; heteroatom such as F, Cl, Br, I; alkyl($C_1$-$C_8$); cycloalkyl($C_3$-$C_8$) without or with substitutions, wherein a substitution is selected from the group consisting of alkyls ($C_1$-$C_8$), cycloalkyls ($C_3$-$C_8$), aryls, heteroaryls; —$OR^{19}$; —$SR^{19}$; —$NR^{19}R^{20}$; —$S(O)R^{19}$; —$S(O)_2R^{19}$; —$S(O)_2NR^{19}R^{20}$; —$C(O)NR^{19}R^{20}$; —$N(R^{19})C(O)R^{20}$; —$N(R^{19})S(O)_2R^{20}$; —$N(R^{19})C(O)N(R^{20}R^{21})$; $N(R^{19})C(O)OR^{20}$; aryl with or without substitution, heteroaryl with or without substitution, aryalkyl with or without substitution, heterocyclyl with or without substitution, heterocyclylalkyl with or without substitution; alkenyl with or without substitution, and alkynyl with or without substitution;

where $R^{19}$, $R^{20}$, and $R^{21}$ are independently chosen from H, alkyl($C_1$-$C_8$), cycloalkyls ($C_3$-$C_8$), aryl with or without substitution, alkylaryl with or without substitutions, heteroaryl with or without substitution, or $R^{16}$, $R^{17}$, and $R^{21}$ can be part of a fused ring containing 0-3 heteroatoms selected from N, O, and S.

2. The compound of claim 1, where Y=S.

3. The compound of claim 1, where Y=O.

4. The compound of claim 1, selected from the group consisting of:
2-(3-fluorophenyl)-4-(piperidin-3-yl-oxy)-thieno[2,3-d]pyridazine-7-carboxylic acid amide, and
2-(3-fluorophenyl)-4-(piperidin-3-yl-thio)-thieno[2,3-d]pyridazine-7-carboxylic acid amide.

5. The compound of claim 1, selected from the group consisting of:
2-(4-chloro-phenyl)-4-(piperidin-3-yl-oxy)-thieno[2,3-d]pyridazine-7-carboxylic acid amide, and
2-(4-chloro-phenyl)-4-(piperidin-3-yl-sulfanyl)-thieno[2,3-d]pyridazine-7-carboxylic acid amide.

6. A pharmaceutical composition comprising a therapeutically effective amount of the compound of claim 1 and a pharmaceutically acceptable excipient.

7. A method for inhibiting the activity of a cancer-related protein-kinase selected from the group consisting of CHK1 and CHK2 in a patient in need thereof, comprising administering to the patient a therapeutically effective amount of the pharmaceutical composition of claim 6.

8. The method according to claim 7, wherein the patient is a human patient.

9. The method according to claim 8, wherein the human patient is suffering from a cancer selected from the group consisting of ovarian cancer, colon cancer, pancreatic cancer, oral cancer, lung cancer, breast cancer, stomach cancer and leukemia.

10. The method according to claim 9, wherein a cytotoxic anti-cancer agent is also administered to the patient.

11. The method according to claim 10, wherein the cytotoxic anti-cancer agent is selected from the group consisting of cisplatin, paclitaxel, pemetrexed, 5-fluorouracil, vinorelbine, oxaliplatin, and gemcitabine.

* * * * *